US 11,975,324 B2

(12) United States Patent
Garstecki et al.

(10) Patent No.: US 11,975,324 B2
(45) Date of Patent: May 7, 2024

(54) MICROFLUIDIC CHIP

(71) Applicant: BACTEROMIC SP. Z O.O., Warsaw (PL)

(72) Inventors: Piotr Garstecki, Warsaw (PL); Pawel Debski, Warsaw (PL); Jaroslaw Ziólkowski, Konstantynów Lódzki (PL); Piotr Knap, Hrubieszów (PL)

(73) Assignee: BACTEROMIC SP. Z O.O., Warsaw (PL)

( * ) Notice: Subject to any disclaimer, the term of this patent is extended or adjusted under 35 U.S.C. 154(b) by 720 days.

(21) Appl. No.: 17/043,236

(22) PCT Filed: Mar. 29, 2019

(86) PCT No.: PCT/EP2019/058102
§ 371 (c)(1),
(2) Date: Sep. 29, 2020

(87) PCT Pub. No.: WO2019/185927
PCT Pub. Date: Oct. 3, 2019

(65) Prior Publication Data
US 2021/0016274 A1 Jan. 21, 2021

(30) Foreign Application Priority Data

Mar. 30, 2018 (PL) .......................... 425106
Aug. 17, 2018 (EP) ..................... 18189586

(51) Int. Cl.
*B01L 3/00* (2006.01)

(52) U.S. Cl.
CPC ... *B01L 3/50273* (2013.01); *B01L 2200/0642* (2013.01); *B01L 2200/0673* (2013.01);
(Continued)

(58) Field of Classification Search
CPC ..... B01L 2200/0642; B01L 2200/0673; B01L 2300/0816; B01L 2300/0864;
(Continued)

(56) References Cited

U.S. PATENT DOCUMENTS 4,018,652 A 4/1977 Lanham
4,318,994 A 3/1982 Meyer et al.
(Continued)

FOREIGN PATENT DOCUMENTS

EP 0785433 A2 7/1997
EP 0903569 A1 3/1999
(Continued)

OTHER PUBLICATIONS

Briskheat Fast Wax Melting for Candle Making Jun. 2023 (Year: 2023).*

(Continued)

*Primary Examiner* — Christine T Mui
*Assistant Examiner* — Jonathan Bortoli
(74) *Attorney, Agent, or Firm* — Browdy and Neimark, PLLC

(57) ABSTRACT

A microfluidic chip for conducting microbiological assays, comprises a substrate in which incubation segments, a sample reservoir and microfluidic channels connecting said sample reservoir with said incubation segments are arranged. Said microfluidic chip further comprise a non-aqueous liquid reservoir for containing non-aqueous liquid wherein said reservoir is connectable via a releasable airtight and liquid-tight valve with said microfluidic channels connecting said sample reservoir with said incubation segments each incubation segment comprises an incubation well (113) connected by a gas-exchange channel (115) to an unvented gas cavity (111).

15 Claims, 13 Drawing Sheets

(52) U.S. Cl.
CPC ............... *B01L 2300/0864* (2013.01); *B01L 2400/0677* (2013.01)

(58) Field of Classification Search
CPC ....... B01L 2400/049; B01L 2400/0677; B01L 3/50273; B01L 2200/0605; C12M 23/16; A01N 43/82; A61K 2039/505; A61K 2039/6056; A61K 2300/00; A61K 2800/10; A61K 31/775; A61K 35/17; A61K 36/06; A61K 39/00; A61K 8/72; A61K 8/86; A61K 9/0019; A61K 9/14; A61P 35/00; A61P 39/06; A61Q 1/02; A61Q 13/00; A61Q 17/02; A61Q 17/04; C07D 271/06; C07D 413/12; C07K 14/521; C07K 14/7158; C07K 16/28; C07K 16/2803; C07K 16/2827; C07K 16/2863; C07K 16/30; C07K 16/3092; C07K 16/32; C07K 2317/56; C07K 2317/622; C07K 2317/732; C07K 2319/30; C07K 2319/33; C07K 2319/95; C08G 65/002; C08G 65/2642; C08G 65/329; C08G 65/34

See application file for complete search history.

(56) References Cited

U.S. PATENT DOCUMENTS

| | | | | |
|---|---|---|---|---|
| RE42,882 E | * | 11/2011 | Kearney | B01J 19/24 138/42 |
| 2002/0119561 A1 | | 8/2002 | Farina et al. | |
| 2003/0152994 A1 | | 8/2003 | Woudenberg | |
| 2004/0219732 A1 | * | 11/2004 | Burns | B01F 33/30 438/200 |
| 2008/0257754 A1 | | 10/2008 | Pugia et al. | |
| 2009/0155128 A1 | | 6/2009 | Peters et al. | |
| 2009/0181411 A1 | | 7/2009 | Battrell et al. | |
| 2011/0020918 A1 | * | 1/2011 | Nassef | G01N 33/5302 435/287.2 |
| 2012/0082599 A1 | | 4/2012 | Weber | |
| 2012/0088263 A1 | * | 4/2012 | Bruno | B01L 3/5025 435/287.1 |
| 2013/0065280 A1 | | 3/2013 | Park et al. | |
| 2015/0072374 A1 | * | 3/2015 | Ng | C12M 47/04 435/287.1 |
| 2016/0354777 A1 | | 12/2016 | Chiu et al. | |
| 2017/0029871 A1 | * | 2/2017 | Ying | G01N 33/54366 |

FOREIGN PATENT DOCUMENTS

| | | |
|---|---|---|
| EP | 1174188 A1 | 1/2002 |
| EP | 1696238 A2 | 8/2006 |
| WO | 2012048096 A2 | 4/2012 |
| WO | 2014052671 A1 | 4/2014 |

OTHER PUBLICATIONS

Heyries et al., "Megapixel digital PCR", Nature America, Inc., pp. 649-852, vol. 8., No. 8 (Aug. 2011).

* cited by examiner

MICROFLUIDIC CHIP

TECHNICAL FIELD

The invention relates to test cards for microbiological assays, especially microbial identification and antimicrobial susceptibility testing (AST). A phenotypical determination of antibiotic resistance requires culturing of isolated microbes (such as from a sample collected from a patient) in the presence of an antibiotic (in this description, 'antibiotic' may mean also a combination of two or more different antibiotics if the determination concerns susceptibility to such combination) and inspecting if microbe growth occurs during the culturing. A determination of a minimum inhibitory concentration (MIC) requires conducting such culturing for different antibiotic concentrations. The addition of specific auxiliary reagents may allow the determination of the resistance mechanism.

In order to conduct an automatic assay of drug susceptibility and determination of the MIC (often combined with identification of the microorganism present in a sample), disposable test cards are used in which culturing of bacteria isolated from a sample is conducted simultaneously in multiple incubation segments. In the context of the present application, whenever "bacteria" are mentioned, the same applies to other microorganisms, such as e.g. single-cell fungi. After preparing of an isolate to be analyzed and placing it on a card, further steps are performed automatically in a dedicated device (a so-called "analyzer"). These steps usually include incubation of the microbes and cyclic optical measurements to detect their growth. Test cards are usually microfluidic chips made of polymer material. A sample is placed into a sample chamber on the chip from where it flows through a network of microfluidic channels to a plurality of independent incubation segments where culturing takes place. The sample flow and filling of incubation segments can be forced by pressure difference, gravity or capillary forces.

One important issue is how to enable the determination of drug-susceptibility and MIC for many antibiotics and their combinations. The cards for these types of tests that are known in the state of the art have just 64 to 136 incubation segments which limits the information obtained in a single test. From the user's viewpoint, it is a fundamental problem since even applying the test intended for a given microbe species gives no guarantee of a result consistent with the guidelines in force in a given country and those set by EUCAST (European Committee on Antimicrobial Susceptibility Testing) or CLSI (Clinical & Laboratory Standards Institute). Often the information on resistance is achieved as so-called antibiotic concentration break points and not the real MIC levels that require conducting a larger number of cultures. This invention aims to solve this and other technical problems related to functionality and correct operation of a test card for microbe identification and drug-susceptibility testing.

STATE OF THE ART

EP 0785433 A2 describes a card for microbiological tests where the sample fills incubation segments under the pressure difference. Before the chip is filled, the sample is in a separate vessel connected with the chip with the use of a hose. Although the need for "placing greater numbers of wells on a card with fixed dimensions" is identified, the chip has only 45 incubation segments, which considerably limits the number of possible assays that can be done in a single test. This is partly because "adding more wells to the card has the potential of increasing the possibility of inter-well cross contamination", which "can result from sample, growth media or reagents diffusing along the fluid channel network from one well to an adjacent well". To prevent this, the separation distance between adjacent wells, as measured along the fluid channels, "is greater than or equal to 2.5 cms ( . . . ) in a card measuring roughly 8.9 cms by 5.7 cms" in a preferred embodiment. The filling procedure requires additional system elements (sample vessels and hoses), which increases operational complexity and the risk of contamination.

A similar chip is disclosed in the patent application EP 1696238 A2. It is filled by a compensation of a pressure around the chip which was previously reduced to 48-62 mbar. The filling process lasts 3-60 s and 90-95% of the sample flows to the incubation segments. In addition, the channels leading to the incubation segments are inclined so that the force of gravity helps in filling them. Channels with circular cross-section are used that, according to the specification, ensure lower resistance of flow and smaller perturbation, than in the case of rectangular channels. To allow the flow of proper sample volume, channels leading to different number of branches (incubation segments) have different cross-sections.

WO 2012/048096 A2 shows a microfluidic chip for AST that has chambers for sample excess so that its volume aspirated into the chip can be greater than a sum of the volumes of the incubation segments and networks of microfluidic channels. Such chambers, called sample excess chambers, over-flow reservoirs or vacuum chambers, placed at the end of blind, unvented fluid distribution channels, are necessitated in several prior art microfluidic chips, including also that of US 2003/0152994 A1 (FIG. 9), by the arrangements of incubation segments in which the inequalities of the length and/or resistance to flow between the microfluidic channels leading from sample source to the respective incubation segments result in unequal filling of the incubation chambers. Sample excess channels of WO 2012/048096 A2 are smaller (i.e. they have a smaller cross-sectional area) than channels leading the sample to the incubation segments so that the filling process is slow enough to ensure a proper filling of the incubation segments. Also, the possible use of non-aqueous liquid (hydrophobic liquid) is described in order to separate incubation segments after filling them with the sample. For this purpose, a wide group of liquids can be used, including mineral oil, olefins, esters, amides, amines, siloxanes, organosiloxanes, ethers, acetals, di-alkyl carbonates, hydrocarbons. The liquid separating incubation segments can be also placed in the external container, in which the suspension of bacteria is stored during a filling process, since the non-aqueous liquid does not mix with such suspension (usually suspension in a broth). The microfluidic chips described above have more incubation segments than the test card disclosed in the application EP 0785433 A2 which is their previous version. However, their number—up to 140, limited i.a. by the approximate volume of a single incubation well of from about 14 µl to about 15 µL by the volume of a single bubble trap of from about 2 µl to about 4 µL, and by the presence of "over-flow reservoirs", is still too small to conduct a wide panel of identification and drug-susceptibility assays.

Separating the chambers in a microfluidic chip with the use of a non-aqueous liquid is discussed in the above-mentioned application regarding the test card and in other publications e.g. the article of K. A. Heyries et al. *Megapixel digital PCR* (Nature Methods Vol 8 No 8, August 2011). In these solutions, non-aqueous liquid is provided to the system from outside. The patent application WO 2014/052671 A1 specifies the device (honeycomb tube) used for biological analysis (multiplex PCR), where an oil chamber with a non-aqueous liquid is a part of the system and it can be fluidically connected with the area of reaction chambers. A similar solution was used in the cartridge for preparing a sample to PCR reaction described in the patent application US 2017/0029871, wherein a common flow-through fluidic channel serves to fill a plurality of wells serially connected thereto. Sample and sealant reservoirs are not arranged in the same microfluidic device but can be connected thereto through valves. The disadvantages of this solution include uneven filling of the wells and increased risk of contamination.

Cards used for automatic microbiological tests conducted in many independent incubation segments are also found in the patent applications EP 0903569 A1 and US 2009/0155128 A1. These chips are filled by gravity or capillary forces, respectively.

US 2012/0082599A1 discloses filling of closed chambers (dead-ends) by applying to the sample a pressure higher than the pressure generated in these closed structures. The latter serves as "a pressure source for pressurizing a front end face in transport direction of the liquid which completely fills the channel leg in cross section", and thereby "prevents unintentional separations of small fluid quantities from the end surface, and leading or trailing of portions of the fluid quantity near the adjacent channel walls due to wetting, and in this manner ensures an exact delimitation of the transported fluid at the front side thereof". In the embodiments discussed in this document the pressure in the closed structures can be additionally controlled by changing their volumes (e.g. by using a flexible membrane or a movable piston) but a filling procedure in which a pressure is lowered before beginning the filing procedure and subsequently raising it to atmospheric pressure is not mentioned. This might be due to the fact that one of the expressed advantages of the invention is the ability to control the flow—by controlling the pressure exerted on the sample, its flow can be forced in both directions or it may be left stationary so that the places where reaction, detection or mixing take place can be separated on the chip.

US2013/0065280A1 describes a chip with substrate incorporating a sample chamber, a distribution channel, reaction chambers, a mixture prevention chamber containing a mixture prevention material to prevent cross-contamination, two valves—one for closing the sample chamber and one for closing the mixture prevention chamber, and an open vent at the end of the distribution channel to drain air therefrom. Since the distribution channel is vented, there is no back-pressure to keep sample from prematurely leaking out of the sample chamber, which necessitates the use of a valve at the outlet of the sample chamber.

US 2016/0354777 A1 discloses fluidic harbours arranged in series of n along main-channel segments, the main-channel segments connected through a bifurcation to a single inlet (FIGS. 10a and 10b) and, also through a bifurcation, with a single outlet (FIG. 10a), or each main channel individually to a large outlet reservoir (FIG. 10b).

Systems for automatic microbiological tests, including determination of antibiotic resistance with dedicated test cards (such as cards disclosed in the patent applications referred to above) are commercially available. These include VITEK, offered by bioMerieux and Phoenix (Becton Dickinson). MicroScan and Sensititre use 96-well plates for AST.

To sum up, cards for automatic AST assays are known in the state of the art. These cards allow culturing to be conducted in multiple incubation segments. After the segments are filled with a sample, chambers can be separated with a non-aqueous liquid in order to prevent cross-contamination. One of their major technical limitations is the number of different test assays which can be conducted simultaneously on the same sample, which does not allow for assessing the real MIC values for the entire range of recommended antibiotics, thus not providing, after a single run time, the comprehensive information needed for timely and accurate treatment of the infected patient.

BRIEF DESCRIPTION OF THE INVENTION

None of the prior art cards teaches a device or method according to the present invention which allows conducting a wide panel of microbiological assays, which requires culturing a microbial culture in as many as several hundred incubation segments, while assuring no contamination between them by the physical separation of sub-volumes of the sample in different segments, where a non-aqueous liquid for preventing cross-contamination is placed in a separate reservoir on the chip. An advantage of the present invention is that in order to perform the process of filling and separating the incubation segments it is only necessary to place the chip in the environment where it is possible to achieve the appropriate pressures (and temperature if a wax valve is used). No external non-aqueous liquid tank or any device to transfer a non-aqueous liquid, e.g. mineral oil or the like, onto the chip is necessary.

The present invention relates to a microfluidic chip that includes multiple independent incubation segments where the incubation and detection of any microbial growth takes place. Up to 640 independent incubation segments are presented in the examples of embodiments but the technology enables even more, for example up to 2,000, independent incubation segments to be provided on a single chip. The chip also has a sample reservoir and a non-aqueous liquid reservoir (such as mineral oil or other liquid that does not mix with water) which can be used to separate the incubation segments from each other to prevent cross-contamination. The non-aqueous liquid can also prevent the evaporation of liquid from the incubation segments. To start an analysis, a sample, which has been loaded into a sample reservoir, is made to flow from the reservoir into the microfluidic structure and fill the individual incubation wells. Then the non-aqueous liquid is released from the reservoir and flows into the microfluidic channels thereby separating the incubation segments from each other—which prevents contamination between the segments. The non-aqueous liquid flow can be controlled by, for example, a heat-sensitive valve (for example made of wax or another low-melting point substance) or other conventional valve known to a person skilled in the art. Preferably the valve is remotely operable. The flow of sample from the reservoir to the incubation segments and the following isolation of the incubation segments from each other by the non-aqueous liquid are achieved by means of pressure difference. To generate this difference, the chip, with a sample in its sample reservoir, is initially placed in an environment (a chamber) where the pressure is subsequently reduced to a certain value $p_0$ lower than the surrounding atmospheric pressure (i.e. a pressure in the surroundings outside a chamber where the chip is placed). This leads to the evacuation of air from the inside of the chip (that is, from the incubation segments and microfluidic channels) through the sample in the sample reservoir and out of the chip, which causes the pressure inside the chip to fall to $p_0$ as well. The pressure in the chamber is then increased which causes the pressures in the system to equalise. The increasing pressure in the chamber compresses the air in the microfluidic system and forces the movement of the sample from the sample reservoir to the incubation segments. Further increases of pressure can, in a following step, be used to drive the flow of non-aqueous liquid. The filling process can be performed in any appropriate filling chamber or container which can be a desiccator, a dedicated instrument for filling one chip or more chips at the same time, or any other instrument able to generate pressures which are lower than the atmospheric pressure.

The present invention also relates to the method of filling the incubation wells of the chip with the sample placed previously in the sample reservoir. The thermodynamic analysis of a process of filling the incubation wells and flow of a non-aqueous liquid separating the incubation segments shows that for the given volumes of the parts of an individual segment, a set of pressures can be selected to ensure the optimum course of these processes. These are the pressures of the air within the microfluidic structure of the chip, hence these are also the pressures that should be generated in a container in which the chip is placed during the filling. The following pressures are needed:

$p_0$, to which the pressure in the filling chamber is reduced;
$p_1 > p_0$, at which the sample flows to the incubation segments;
$p_2 > p_1$, at which the non-aqueous liquid flows to the microfluidic channels.

These pressures can be used to ensure a correct filling process after which the section of the incubation segment intended to receive a portion of the sample (called an "incubation well") preferably contains substantially no non-aqueous liquid or air, there is no contamination between the incubation segments and the deviation in volume of the sample sub-volumes contained in the incubation segments on the chip that are most distant from the sample reservoir is reduced.

Preferred aspects of the invention are as follows:

A microfluidic chip for conducting microbiological assays, comprising a substrate in which incubation segments each with an inlet, a sample reservoir with an outlet and microfluidic channels connecting the outlet of said sample reservoir with each inlet to said incubation segments are arranged, wherein said microfluidic chip further comprises a non-aqueous liquid reservoir for containing non-aqueous liquid wherein said reservoir is connectable via a releasable airtight and liquid-tight valve with said microfluidic channels.

A chip according to the previous aspect, wherein the number of incubation segments is equal to or greater than 100 incubation segments, preferably equal to or greater than 128 incubation segments, more preferably equal to or greater than 320 incubation segments, even more preferably equal to or greater than 640 incubation segments, and most preferably equal to or greater than 1280 incubation segments.

A chip according to any of the previous aspects wherein said microbiological assay belongs to a group including identification of microorganism, determination of susceptibility to an antibiotic or a combination of antibiotics, determination of a minimum inhibitory concentration (MIC) or detecting of a mechanism of antibiotic resistance.

A chip according to any of the previous aspects wherein said chip is made of a polystyrene, polycarbonate, poly (methyl methacrylate), cyclic olefin polymer or cyclic olefin copolymer.

A chip according to any of the previous aspects wherein said valve is a heat-sensitive valve.

A chip according to any of the previous aspects wherein said valve is a heat-sensitive wax valve which contains wax which melts at a temperature greater than or equal to 37° C.

A chip according to any of the previous aspects wherein the incubation segments are arranged, preferably, in a fractal manner in which the respective microchannels connecting each of the incubation segments to the sample reservoir are substantially equally long and/or have the same resistance to flow.

A chip according to any of the previous aspects wherein the shortest distance between two adjacent incubation segments, measured along the microfluidic channels connecting these segments, is less than or equal to 10 mm, preferably less than or equal to 8 mm, more preferably less than or equal to 7 mm.

A chip according to any of the previous aspects wherein the volume of the sample reservoir is at least three times larger than the total volume of the incubation wells.

A chip according to any of the previous aspects wherein the volume of the non-aqueous liquid reservoir is at least two times larger, and preferably at least three times larger, than the total volume of the microfluidic channels leading from the sample reservoir to the incubation segments.

A chip according to any of the previous aspects wherein the sample reservoir is of elongated shape and its maximum longitudinal dimension is greater than or equal to 30 mm, preferably greater than or equal to 40 mm, more preferably greater than or equal to 50 mm.

A chip according to any of the previous aspects wherein the sample reservoir has an inlet end and an outlet end wherein the outlet end is wider than the inlet end and/or the width of the outlet end of the sample reservoir perpendicular to the longitudinal axis of the sample reservoir is greater than or equal to 5 mm, preferably greater than or equal to 7 mm, more preferably greater than or equal to 10 mm.

A chip according to any of the previous aspects wherein the sample reservoir has at least a first side wall and an opposite second side wall wherein at least one projection protrudes from said first side wall wherein width of the projection measured in a direction perpendicular to said side wall is greater than or equal to 1 mm, preferably greater than or equal to 2 mm, more preferably greater than or equal to 3 mm, and/or wherein the shortest distance between the projection's distal end and the opposite side wall is preferably greater than or equal to 3 mm, more preferably greater than or equal to 4 mm.

A chip according to any of the previous aspects wherein the non-aqueous liquid reservoir has an inlet end and an outlet end and the width of the outlet end is narrower than the width of the inlet end.

A chip according to any of the previous aspects wherein the width of the non-aqueous liquid reservoir at its widest point is greater than or equal to 4 mm, preferably greater than or equal to 5 mm, more preferably greater than or equal to 6 mm.

A chip according to any of the previous aspects wherein the distance between the sample reservoir outlet opening and the lowest point of the sample reservoir ($d_1$ in FIG. 12), and the distance between the opening through which the non-aqueous liquid enters the sample reservoir and the nearest side wall of the sample reservoir ($d_2$ in FIG. 12) are each equal to or less than 3 mm and more preferably equal to or less than 2 mm.

Further aspects of the invention relate to:

A method of filling of the incubation segments in a microfluidic chip according to any of the previous aspects including the following steps in order:
- a. providing in said non-aqueous liquid reservoir a non-aqueous liquid,
- b. inputting a sample to the sample reservoir,
- c. placing a chip in a hermetically-sealed container separated from its surroundings,
- d. reducing the pressure in said container to a value $p_0$,
- e. increasing the pressure in said hermetically-sealed container to a value $p_1$, at which sample flows from a sample reservoir to the microfluidic channels connecting said sample reservoir with the incubation segments and further into said incubation segments,
- f. activating the valve to open a flow path from said non-aqueous liquid reservoir to said microfluidic channels connecting said sample reservoir with said incubation segments, and
- g. further increasing the pressure in said hermetically-sealed container to a value $p_2$, to force said non-aqueous liquid to flow into the microfluidic channels connecting the sample reservoir and said non-aqueous liquid reservoir with the incubation segments;
- h. optionally subsequently further increasing the pressure in said hermetically-sealed container to ambient atmospheric pressure $p_{atm}$, wherein $p_0$ ranges between $$\frac{NV_D}{N(V_A+V_B+V_C+V_D)+V_{in}+V_{total}}p_{atm} \text{ and}$$

$$\frac{N(V_D+V_C)}{N(V_A+V_B+V_C+V_D)+V_{in}+V_{total}}p_{atm},$$

$p_1$ ranges between $$\frac{NV_D}{N(V_A+V_C+V_D)+V_{in}+V_{total}}p_{atm} \text{ and}$$

$$\frac{NV_D}{NV_D+V_{in}+V_{total}}p_{atm}$$

and $p_2$ ranges between $$\frac{NV_D}{N(V_A+V_C+V_D)+V_{in}}p_{atm}$$

and $p_{atm}$,
- where $p_{atm}$ denotes ambient atmospheric pressure outside said hermetically-sealed container, N—number of incubation segments in said chip, $V_A$—volume of an inlet channel of an incubation segment, i.e. the channel connecting main microfluidic network with the incubation well, $V_B$—volume of an incubation well, $V_C$—volume of a gas exchange channel connecting the incubation well and a gas cavity, $V_D$—volume of the gas cavity, $V_{in}$—volume of an intake channel of the main microfluidic network, i.e. the channel leading from the sample reservoir to the first branch of the main microfluidic network, $V_{total}$—a total volume of the network of microfluidic channels leading from the sample reservoir to the incubation segments excluding the said intake channel.

A method according to any of the previous method aspects wherein after step g or step h, the microfluidic chip is permanently sealed and the interior of the chip separated from its surroundings.

A method according to any of the previous method aspects wherein said non-aqueous liquid has viscosity greater than or equal to 20 cP, preferably greater than or equal to 50 cP according to ASTM D7279.

DETAILED DESCRIPTION OF INVENTION

Structure of the Chip

Figure 1:
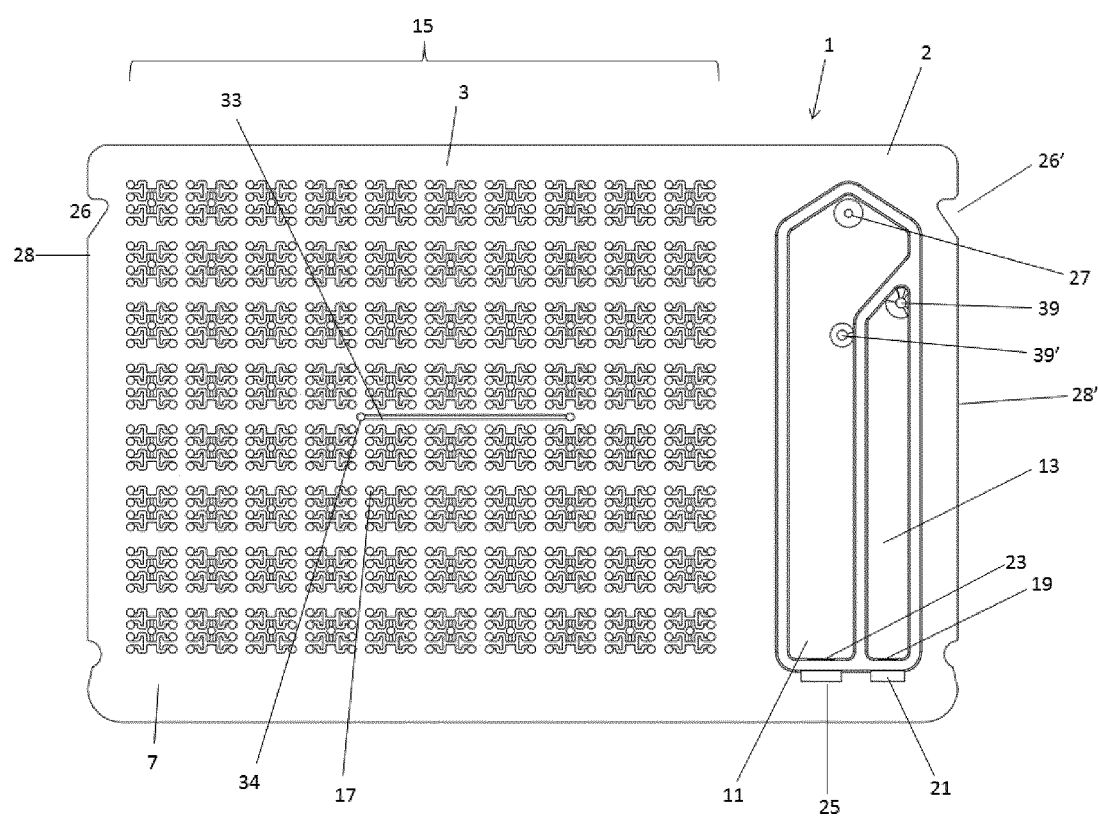
FIG. 1 shows a schematic plan view of a first major surface of a chip according to the present invention.
Figure 2:
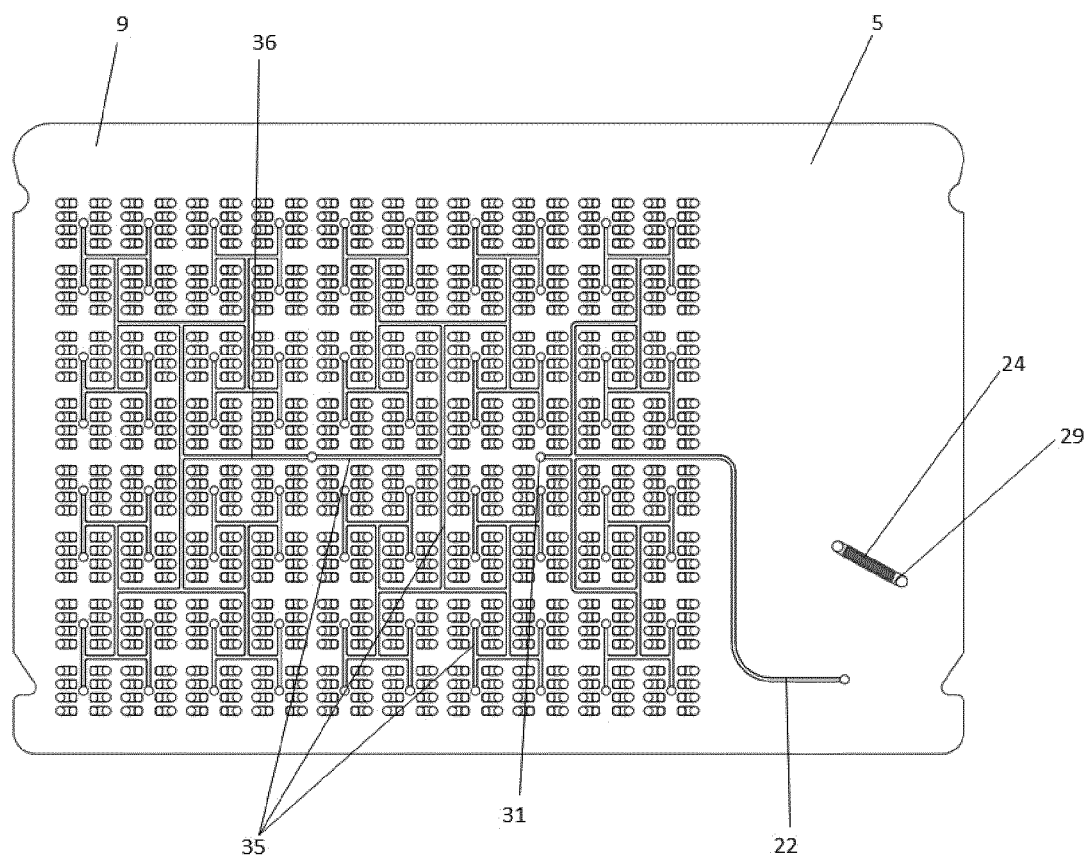
FIG. 2 shows a schematic plan view of the second major surface of the chip of FIG. 1.

FIGS. 1 and 2 show schematically a first embodiment of a microfluidic chip 1 in accordance with the present invention. The chip is formed of a substrate 2. The substrate is preferably planar with a first major face 3 and a, preferably parallel, second major face 5. The substrate may be made of any liquid and vapour impermeable material, for example a polymer, metal or glass. The thickness of the substrate is preferably equal to or greater than 1.5 mm and less than or equal to 3.00 mm. The substrate may be manufactured as one part (by for example injection moulding or milling a polymer) or may be composed of two parts i.e. a base plate (with the incubation segments and the microfluidic channels) and the reservoirs which are joined together by means of bonding methods known in the state of the art. The surface of the first major face is covered by a first layer 7 of impermeable, substantially transparent material and the surface of the second major surface is covered by a second layer 9 of impermeable, substantially transparent material. Preferably each of these layers is equal to or greater than 0.05 mm thick and less than or equal to 0.15 mm thick.

These layers prevent the entry or release of unwanted gas and liquids from the structures (described later) formed in the substrate while permitting light to pass through the incubation wells—thus allowing optical examination of the samples in the incubation wells. Microfluidic chip 1 includes a sample reservoir 11 for receiving and storing a sample for analysis (for example an inoculum of bacteria), a non-aqueous liquid reservoir 13 for receiving and storing a non-aqueous liquid, and an incubation segment area 15 comprising a plurality of incubation segments 17 in each of which a portion of the sample can be cultured.

The non-aqueous liquid reservoir 13 can be supplied with a non-aqueous liquid through a non-aqueous liquid inlet passage 19 which leads through the substrate to the non-aqueous liquid reservoir from a non-aqueous liquid inlet opening 21 on the first major face.

The sample reservoir 11 can be supplied with a sample, for example an inoculum of bacteria for analysis, through a sample inlet passage 23 which leads through the substrate to the sample reservoir from a sample inlet opening 25 on the first major face.

Sample reservoir has an outlet opening 27 which leads to a channel 22 formed in the substrate on the second major face of the chip. Channel 22 leads to a passage 31 formed in the substrate in the incubation segment area 15. This passage passes through the substrate and connects channel 22 with a channel 33 formed in the first major face of the substrate. Channel 33 is connected via a further passage 34 to a network of microfluidic channels 35 which lead to incubation segments 17 formed in the substrate. Preferably the microfluidic channels have a quadratic cross-section. Preferably the microfluidic channels have a cross-sectional area which is equal to or greater than 0.05 square mm and less than or equal to 1 square mm, more preferably the microfluidic channels have a cross-sectional area which is equal to or greater than 0.16 square mm and less than or equal to 0.64 square mm.

Non-aqueous liquid reservoir has an outlet opening 39 which leads to channel 29 and further via this channel to an outlet opening 39' through which the non-aqueous liquid enters the sample reservoir. Channel 29 can be temporarily blocked by a wax valve 24 or other, preferably remotely-activated valve, located in the channel 29 which, when closed, prevents the non-aqueous liquid from flowing through channel 29. When valve 24 is open, for example by heating in the case of a wax valve, the non-aqueous liquid can flow through channel 29 and into the sample reservoir.

The chip preferably has notches 26, 26' formed in two or more edges 28, 28' to allow the chip to be hooked onto the edges of a basket (not shown) used for carrying the chips in and/or a container in an analyser device (not shown) such that the sample inlet opening 25 is above the sample reservoir outlet opening 27 during filling.

The incubation segments area includes a plurality of incubation segments 17 and microfluidic channels 35 which can lead the sample to these incubation segments. The sample is transported to the individual incubation segments by the interconnecting network of channels (22, 33, 35), also referred to as a "main microfluidic network", formed on the two major faces of the substrate of the chip which improves effective use of space on the chip and hence allows more segments to be accommodated in a single chip. The chip shown in the figure has 640 independent incubation segments in which the culturing of bacteria (or other microorganisms) may take place.

Figure 3:
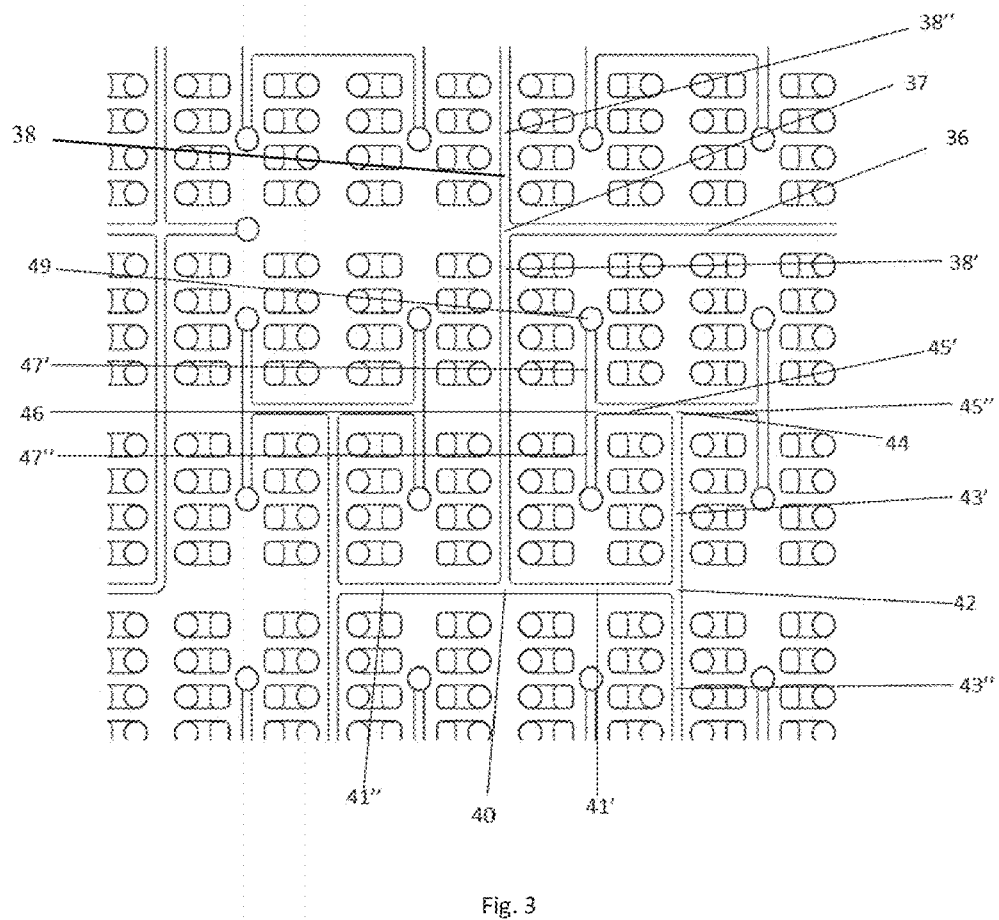
FIG. 3 shows a schematic view of the detailed structure of the channels in the second major surface of the chip of FIG. 1.

During the filling process, the sample located at the beginning in the sample reservoir flows to the channel 22. The channel ends with a passage 31 through which the sample enters the channel 33 on the first major face of the chip. This channel conducts the sample to the network of microfluidic channels 35. In this embodiment of the invention the network of microfluidic channels is arranged as a fractal structure of channels leading to the incubation segments in which the sample is further divided into equal portions that enter smaller microchannel structures via branched channels. More specifically, the chip in the FIGS. 1-2 consists of two asymmetric parts with 128 and 512 incubation segments. Preferably the resistance to flow for each pathway from the sample reservoir to an individual incubation segment is substantially the same for every such pathway so that the amount of sample reaching each incubation segment will be substantially the same. FIG. 3 shows an example of one path through these connected microchannels—a portion of the sample flows down channel 36 until it reaches a T-junction 37 with a secondary channel 38. Here substantially half of the sample flows in one direction (e.g. to the left) in the first branch 38' of the secondary channel and the other half of the sample flows in the opposite direction (e.g. to the right) in the second branch 38". Each of these branches in turn leads to a T-junction 40 with a tertiary channel 41.

At the T-junction 40 substantially half of the sample flows in one direction (e.g. to the left) in the first branch 41' of the tertiary channel and the other half of the sample flows in the opposite direction (e.g. to the right) in the second branch 41". Each of these branches in turn leads to a T-junction 42 with a quaternary channel 43', 43".

At the T-junction substantially half of the sample flows in one direction (e.g. to the left) in the first branch 43' of the quaternary channel and the other half of the sample flows in the opposite direction (e.g. to the right) in the second branch 43". Each of these branches in turn leads to a T-junction 44 with a quinary channel 45', 45".

At the T-junction substantially half of the sample flows in one direction (e.g. to the left) in the first branch 45' of the quinary channel and the other half of the sample flows in the opposite direction (e.g. to the right) in the second branch 45". Each of these branches in turn leads to a T-junction 46 with a senary channel 47.

Figure 4:
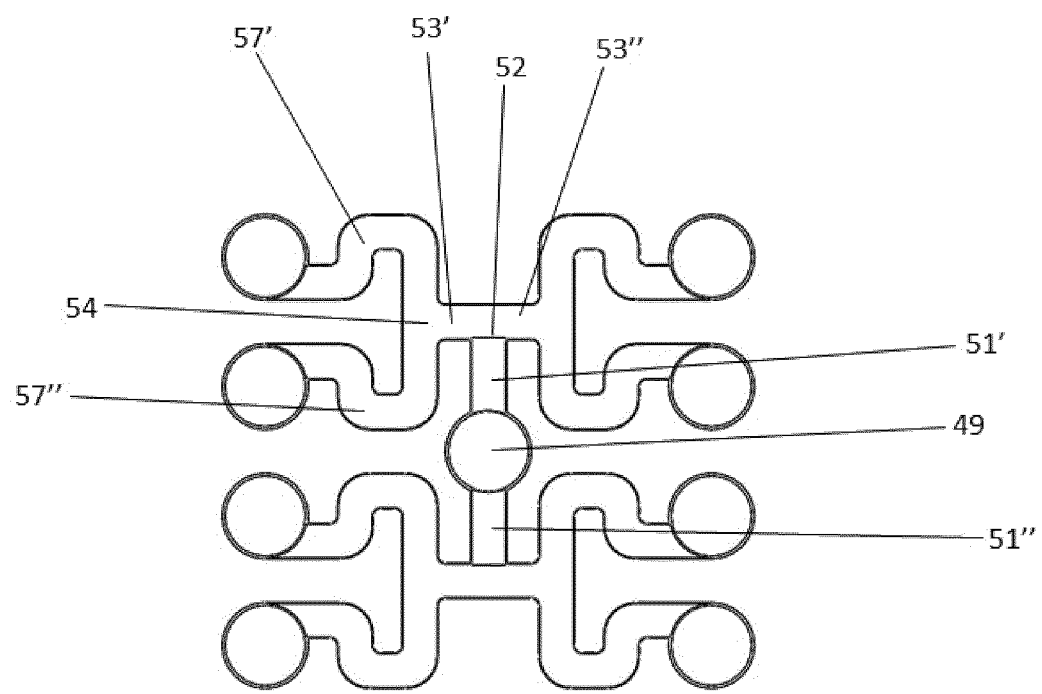
FIG. 4 shows an enlarged schematic view of section of the first major surface of the chip including 8 incubation segments.

Here substantially half of the sample flows in one direction (e.g. to the left) in the first branch 47" of the senary channel and the other half of the sample flows in the opposite direction (e.g. to the right) in the second branch 47'. Each of these branches in turn lead to a transport passage 49 which penetrates the substrate (but not the layers of impermeable material) and leads the sample to a septenary channel 51 which has two branches 51', 51" each of which extend, as shown in FIG. 4, in the surface of the first major face of the substrate, in two opposite directions from the transport passage to a T-junction 52 with a delivery channel 53.

At the T-junction 52 substantially half of the sample flows in one direction (e.g. to the left) in the first branch 53' of the delivery channel and the other half of the sample flows in the opposite direction (e.g. to the right) in the second branch 53". Each of these branches in turn leads to a T-junction 54 with a splitter channel 57.

At the T-junction 54 substantially half of the sample flows in one direction (e.g. to the right) into an inlet channel 57' of a first associated incubation segment 17' and the other half of the sample flows in the opposite direction (e.g. to the left) into an inlet channel 57" of a second associated incubation segment 17".

Each incubation segment 17 includes an incubation well 113—a chamber where a subvolume of the sample is located during incubation—connected by a gas-exchange channel 115 to its associated unvented gas cavity 111—comprising a chamber filled with air, or any other gas or gas mixture, necessary for microbial growth. The unvented gas cavity prevents contamination of the sample and the loss of sample or sample fluid by evaporation while providing gas which can be used by cells in the incubation chamber.

Once the sample has entered the incubation well the valve is operated to release the non-aqueous liquid, for example, the wax valve is heated and the wax melted, which releases the non-aqueous liquid from reservoir 13. This non-aqueous liquid flows via the same paths as the sample remaining in the microfluidic channels until it reaches the splitter channel 57', 57" which it at least partly fills, thereby providing a barrier which prevents gas or aqueous fluids from moving from one incubation segment to another. Preferably the viscosity—at the temperature used for the loading of the chip—of the non-aqueous liquid is greater than or equal to 20 cP, more preferably greater than or equal to 50 cP measured according to the ASTM method ASTM D7279.

Embodiment of a chip presented in FIGS. 1-4 has overall dimensions of 128×85 mm and thickness of its substrate is equal to 2.2 mm. But any sizes are possible provided that they enable accommodating of the desired number of the incubation segments and fulfilling other criteria described in this description. For example, a chip with 128 incubation segments was designed having overall dimensions of 85.5× 49.7 mm. Also chip with larger size can be manufactured as long as it is handy for the user which is a desired property of a diagnostics chip.

Explanation of a Chip Operation

In the following description the symbol $p_{atm}$ refers to the ambient atmospheric pressure in the surroundings outside of a device in which the incubation segments are filled according to the method described below.

Chip with Series Connection of the Incubation Segments

Figure 5:
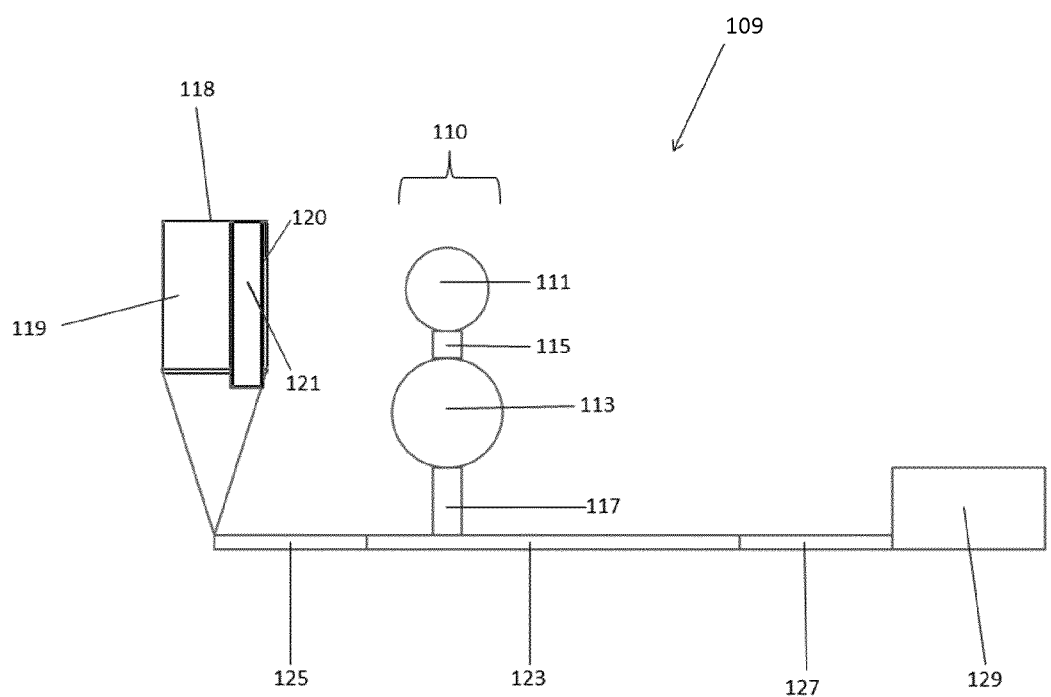
FIG. 5 shows a schematic representation of a chip with series connection of incubation segments.

A chip with a series connection between incubation segments is presented in the following. A chip 109 with a series connection of incubation segments to the sample reservoir is schematically represented in FIG. 5. For the sake of simplicity, FIG. 5 shows only one incubation segment branching off from the main microfluidic channel, although preferably many incubation segments branch off from it. They can be located on either side of the main channel. In addition, the chip can include many such main channels. A reservoir 118 includes a portion 119 for containing a sample and a reservoir 120 for non-aqueous liquid 121 which can be isolated from the portion 119 by a valve (not shown). Each incubation segment 110 comprises 4 elements i.e. a gas cavity 111 of volume $V_D$, an incubation well 113 of volume $V_B$, a microfluidic channel 115 of volume $V_c$ connecting these two parts, also referred to as a gas exchange channel, and a microfluidic channel 117 of volume $V_A$, also referred to as an inlet channel of the incubation segment, leading to the incubation well from a main channel 123. Thus, the total volume of the incubation segment $V_{ABCD}$ is equal to $V_A+V_B+V_c+V_D$. The main channel 123 of volume $V_{KG}$ is connected to the reservoir 118 by an intake channel 125 of volume $V_{in}$ and connected to a vacuum chamber 129 of volume $V_{vac}$ via a channel 127 of volume $V_{out}$. Therefore, the overall volume of the main channel $V_{oKG}$ is the sum of the respective volumes i.e. $V_{oKG}=V_{in}+V_{KG}+V_{out}$. In the case of a chip with series connection of incubation segments, the volume $V_{in}$ of the intake channel of the main microfluidic network is defined as a volume of the part of the main microfluidic network between the sample reservoir outlet and a point at which a first (proximal) inlet channel 117 of an incubation segment branches off from the main microfluidic network.

Chip with a Fractal Geometry

Figure 6:
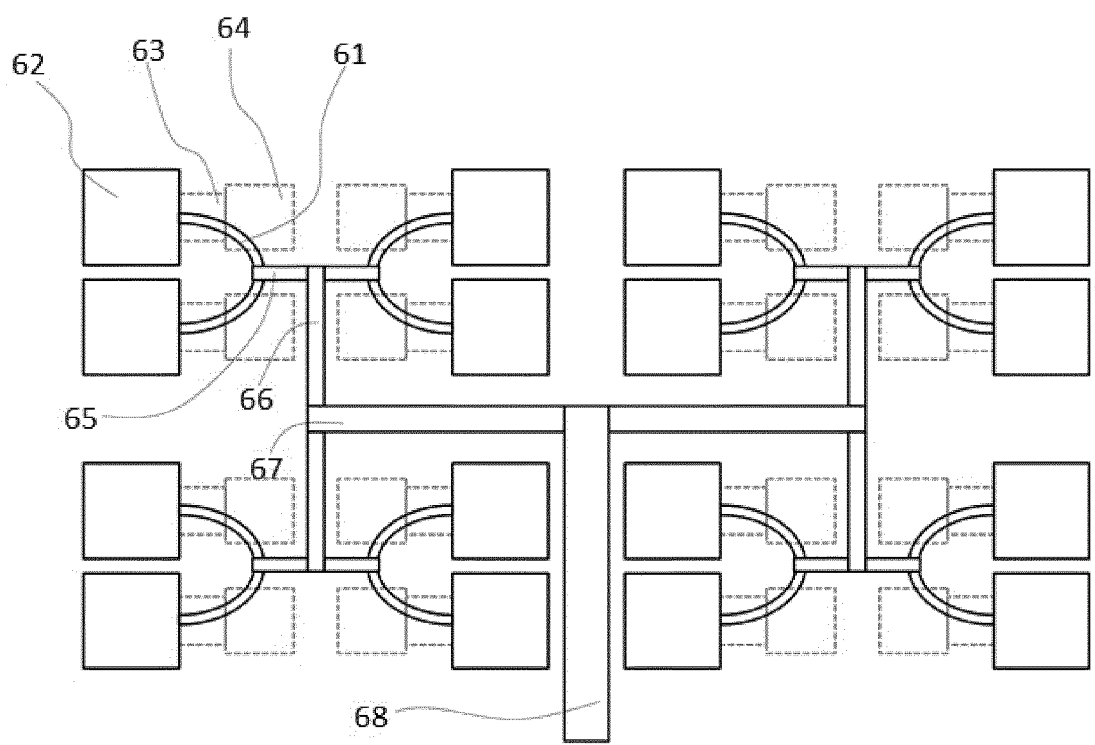
FIG. 6 shows schematically a plan view of a section of a chip with fractal geometry including 16 incubation segments.
Figure 7:
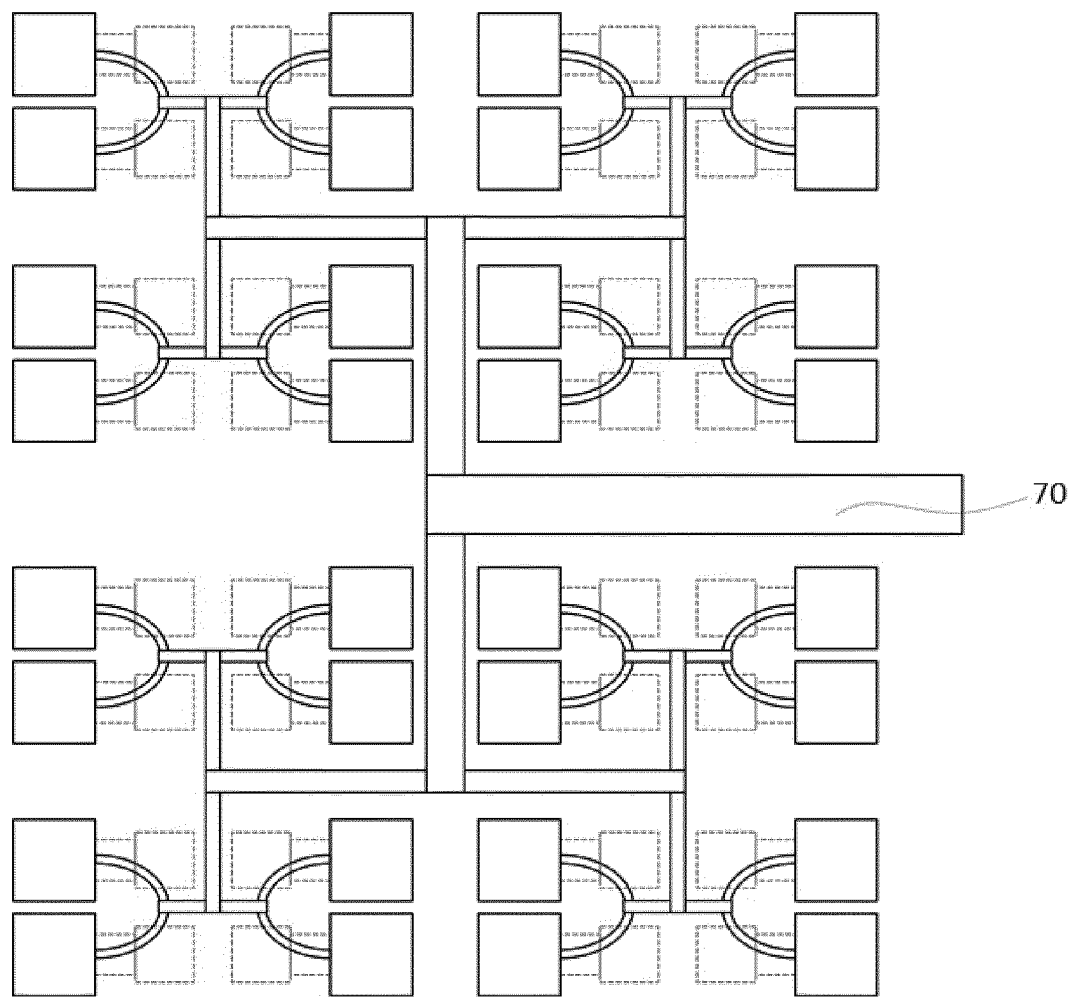
FIG. 7 shows schematically a plan view of a section of a chip with fractal geometry including 32 incubation segments.
Figure 8:
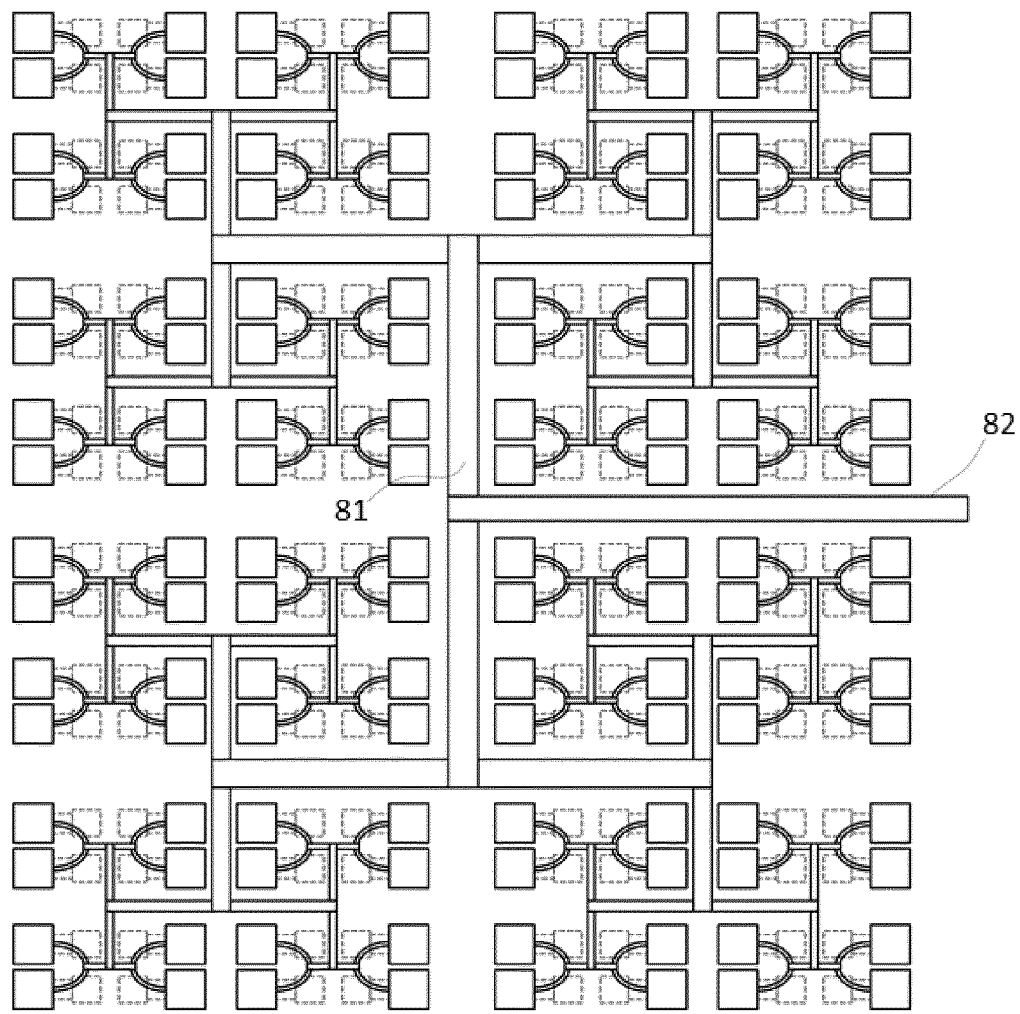
FIG. 8 shows schematically a plan view of a section of a chip with fractal geometry including 128 incubation segments.

FIG. 6, FIG. 7 and FIG. 8 show schematically the parts of a chip with fractal geometry including 16, 32 and 128 incubation segments respectively. In the FIG. 6 the elements of each incubation segment are marked. These are: incubation well (62) of volume $V_B$, gas cavity (64) of volume $V_D$, and the microfluidic channels 61 (inlet channel of the incubation segment of volume $V_A$) and 63 (gas exchange channel of volume $V_C$). Preferably, the gas cavity 64 is located under the inlet channel 61 leading the sample to the incubation well and separated from the inlet channel by a predetermined thickness of substrate material. Having the inlet channel overlapping the gas cavity allows more efficient use of a space on the chip so that with chips of easily-handled sizes (e.g. standard sized microplates of approximately 128 mm×85 mm), a large number of closely spaced incubation segments (up to 640 or more) can be located on the chip which improves its functionality by allowing more bacterial cultures to be conducted during a single test. It should be noted that the number of the independent reaction wells is the main factor limiting a functionality of the prior art AST test cards. The possibility of accommodating such a large number of incubation segments on a single chip enables the acquisition of comprehensive information on the drug susceptibility of the bacteria in the sample (i.e. by permitting the testing of more antibiotics or their combinations for a possible resistance, determining of a true MIC which requires conducting a bigger number of cultures than determining the antibiotic concentration break points, possible finding of a resistance mechanism). In this respect the incubation segment enables obtaining unique properties which significantly exceed the properties of the AST test cards known in the state of the art. Preferably, as shown most clearly in FIGS. 6-8, in order to utilize the area of the chip efficiently, the microfluidic channels 63 between the incubation well and the gas cavity are formed in one major face of the substrate and some or all of the other microfluidic channels formed in the opposite major face of the substrate. The channels 65, 66, 67 and 68 lead a sample to 2, 4, 8 and 16 incubation segments, respectively. Similarly, the channels 70, 81 and 82 lead a sample to 32, 64 and 128 incubation segments respectively.

Calculations

1. Mathematical model and conditions for correct functioning of a chip:
 1.1. Assumptions regarding geometry:
  1.1.1. Rank of a fractal equals i means $N=2^i$ of the incubation segments $V_{ABCD}$.
  1.1.2. The shape of an inlet channel of an incubation segment is changed in comparison with a chip with a series connection.
  1.1.3. A base cell consists of two incubation segments of volume $V_{ABCD}$. A channel $V_k$ leads to the number k of incubation segments.
  1.1.4. There is no vacuum chamber.
 1.2. Steps during filling of the incubation segments:
  1.2.1. Lowering of a pressure to the value $p_0$.

$$RTn_g = p_0(2^i V_{ABCD} + V_{in} + \Sigma_{j=1}^{i} 2^{i-j} V_{2j}).$$

1.2.2. Causing a sample flow from the sample reservoir to the microfluidic system by changing the pressure to the exemplary preferred pressure $p_1$. As a result there will be the following volume of a sample in the microfluidic system: $2^i(\frac{1}{2}V_A + V_B + \frac{1}{2}V_C)$ $$p_1 = p_0 \frac{2^i(V_A + V_B + V_C + V_D) + V_{in} + \sum_{j=1}^{i} 2^{i-j} V_{2^j}}{2^i\left(\frac{1}{2}V_A + \frac{1}{2}V_C + V_D\right) + V_{in} + \sum_{j=1}^{i} 2^{i-j} V_{2^j}}.$$

1.2.3. Forcing a non-aqueous liquid to flow into the microfluidic channels connecting the sample reservoir and said non-aqueous liquid reservoir with the incubation segments at the exemplary preferred pressure $p_2$. Then the channels of the main microfluidic network are fed with a volume $\sum_{j=1}^{i} 2^{i-j} V_{2^j}$ of the non-aqueous liquid and the incubation segments are separated.

$$p_2 = p_1 \frac{2^i\left(\frac{1}{2}V_A + \frac{1}{2}V_C + V_D\right) + V_{in} + \sum_{j=1}^{i} 2^{i-j} V_{2^j}}{2^i\left(\frac{1}{2}V_A + \frac{1}{2}V_C + V_D\right) + V_{in}}.$$

1.2.4. Causing further flow into the microfluidic system of the non-aqueous liquid at the pressure $p_3 = p_{atm}$. This allows compressing air in the gas cavities $V_D$ and filling the entire incubation wells with a sample.

$$p_3 = p_2 \frac{2^i\left(\frac{1}{2}V_A + \frac{1}{2}V_C + V_D\right) + V_{in}}{2^i\left(V_D + \frac{1}{2}V_C\right)}.$$

1.3. Summary:
  1.3.1. Exemplary preferred volume formulas for gas $V_{air}$, sample $V_w$ and non-aqueous liquid $V_o$ contained in the microfluidic structure of the chip after filling at the temperature $T_1 = 20°$ C.:

$V_{air} = 2^i V_D$, $V_w = 2^i(\frac{1}{2}V_A + 1 V_B + \frac{1}{2}V_C)$, $V_o > 2^i V_A + V_{in} + \sum_{j=1}^{i} 2^{i-j} V_{2^j}$.

1.3.2. The volume formulas at the temperature $T_2 = 37°$ C.:

$V_{air} = 1.07 \cdot 2^i V_D \approx 2^i(V_D + \frac{1}{2}V_C)$, $V_w = 2^i(\frac{1}{2}V_A + 1 V_B + \frac{1}{2}V_C)$, $V_o \approx 2^i(\frac{1}{2}V_A) + V_{in} + \sum_{j=1}^{i} 2^{i-j} V_{2^j}$.

1.3.3. Optimal pressure values:

$$p_0 = p_3 \frac{2^i\left(V_D + \frac{1}{2}V_C\right)}{2^i(V_A + V_B + V_C + V_D) + V_{in} + \sum_{j=1}^{i} 2^{i-j} V_{2^j}},$$

$$p_1 = p_3 \frac{2^i\left(V_D + \frac{1}{2}V_C\right)}{2^i\left(\frac{1}{2}V_A + \frac{1}{2}V_C + V_D\right) + V_{in} + \sum_{j=1}^{i} 2^{i-j} V_{2^j}},$$

$$p_2 = p_3 \frac{2^i\left(V_D + \frac{1}{2}V_C\right)}{2^i\left(\frac{1}{2}V_A + \frac{1}{2}V_C + V_D\right) + V_{in}},$$

where:
$\sum_{j=1}^{i} 2^{i-j} V_{2^j}$ is a sum of the volumes of all channels leading from the sample reservoir to the incubation segments (with the exception of the intake channel $V_{in}$);

$V_{in}$ is a volume of an intake channel of the main microfluidic network, i.e. the channel leading from the sample reservoir (and non-aqueous liquid reservoir) to a fractal microfluidic structure of the chip, i.e. to the first branching point;

Therefore $V_{in} + \sum_{j=1}^{i} 2^{i-j} V_{2^j}$ is the sum of the volumes of all channels leading from the sample reservoir to the incubation segments;

$p_3$ is the atmospheric pressure.

1.4. Input data:

$p_3 = p_{atm}$, $V_A = 0.197$ μL, $V_B = 2.45$ μL, $V_C = 0.174$ μL, $V_D = 1.17$ μL, $i = 7$, $V_2 = 1 \cdot 0.5 \cdot 0.5$ μL $= 0.25$ μL, $V_4 = 2 \cdot 0.5 \cdot 0.5$ μL $= 0.5$ μL, $V_8 = 4 \cdot 0.5 \cdot 0.5$ μL $= 1$ μL, $V_{16} = 4 \cdot 0.5 \cdot 0.5$ μL $= 1$ μL, $V_{32} = 8 \cdot 0.5 \cdot 0.5$ μL $= 2$ μL, $V_{64} = 8 \cdot 0.5 \cdot 0.5$ μL $= 2$ μL, $V_{128} = 16 \cdot 0.5 \cdot 0.5$ μL $= 4$ μL, $\sum_{j=1}^{i} 2^{i-j} V_{2^j} = 72$ μL, $V_{in} = 4$ μL.

1.4.1. Results—the optimal values of pressure which allow correct functioning of the chip with the above volumes and ratios between the volumes of the different sections:

$p_3 = P_{atm} = 1013.25$ mbar, $p_0 = 0.274 p_3 = 278$ mbar, $p_1 = 0.645 p_3 = 653$ mbar, $p_2 = 0.906 p_3 = 918$ mbar.

Figure 9:
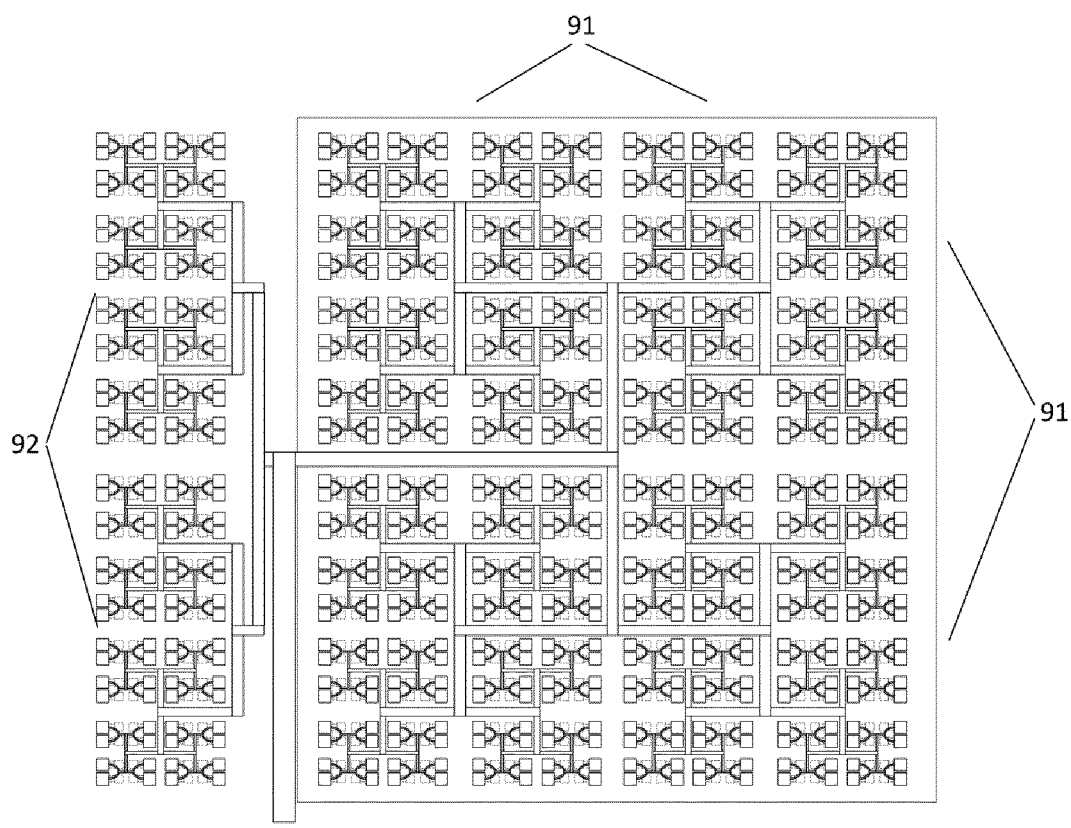
FIG. 9 shows schematically a plan view of a chip with asymmetric fractal geometry with 640 incubation segments.

Chip with a Fractal Geometry and Asymmetric Branches
  1.1. Geometry of the chip
  An example of an asymmetric fractal chip is shown in FIG. 9. The chip includes 640 incubation segments which consists of the following structures
    i) 4 parts with 128 incubation segments (described above)—shown by 91 in FIG. 9,
    ii) 2 parts with 64 incubation segments—shown by 92 in FIG. 9.
  1.2. Mathematical and design assumptions:
    1.2.1. All incubation segments are identical and indistinguishable (from a model point of view).
    1.2.2. A partial volume of all supplying channels per a single incubation segment (quotient of a sum of the volumes of all channels leading to an incubation segment, including channel $V_{in}$, and a number of the incubation segments which share these channels) is constant. This is calculated for each incubation segment by adding up, for each microfluidic channel section leading from the sample reservoir to the incubation segment in question, a quotient of the microfluidic channel section's volume and a number of incubation segments to which it leads.

1.2.3. All incubation segments are connected in parallel. This means that there can be only forks of the channels (or, more generally, each channel can only split into two branches at junctions) without any series connections.

The above-mentioned conditions lead to a fractal distribution of incubation segments and a uniform partition of a sample and non-aqueous liquid.

1.3. Mathematical model.

The assumptions from point 1.2 do not change the values of pressure derived in the previous subsection because they depend only on the volumes occupied by a sample and air in the incubation segments which are the same. Hence, we obtain the following values of a pressure:

i) Optimal initial pressure:

$$p_0 = p_3 \frac{N\left(V_D + \frac{1}{2}V_C\right)}{N(V_A + V_B + V_C + V_D) + V_{in} + V_{total}},$$

Where $V_{total}$ means a sum of the volumes of all channels leading from the sample reservoir to the incubation segments without the intake channel $V_{in}$ and N means total number of the incubation segments.

ii) The optimal pressure required for causing the flow of sample into the incubation segments:

$$p_1 = p_3 \frac{N\left(V_D + \frac{1}{2}V_C\right)}{N\left(\frac{1}{2}V_A + \frac{1}{2}V_C + V_D\right) + V_{in} + V_{total}}.$$

iii) The optimal pressure required for separating the incubation segments with a non-aqueous liquid:

$$p_2 = p_3 \frac{N\left(V_D + \frac{1}{2}V_C\right)}{N\left(\frac{1}{2}V_A + \frac{1}{2}V_C + V_D\right) + V_{in}}.$$

1.4. Conclusions—an optimization of a geometry of the asymmetric fractal chip is necessary to ensure its correct functioning:

1.4.1. In the first fork 100 (in FIG. 10), the volume of a sample that flows into the incubation segments at the right side should be correspondingly larger than the volume of a sample which flows into the incubation segments at the left side. A ratio of these volumes is equal to the ratio of the numbers of the incubation segments at the right side and the left side.

$$\frac{V_{sample_{right}}}{V_{sample_{left}}} = \frac{N_{right}}{N_{left}}.$$

1.4.2. Assumption above imposes an analogous ratio of a volume of air and therefore of a volume of the channels at the right side and the left side.

$$\frac{V_{channels_{right}}}{V_{channels_{left}}} = \frac{N_{right}}{N_{left}}.$$

Figure 10:
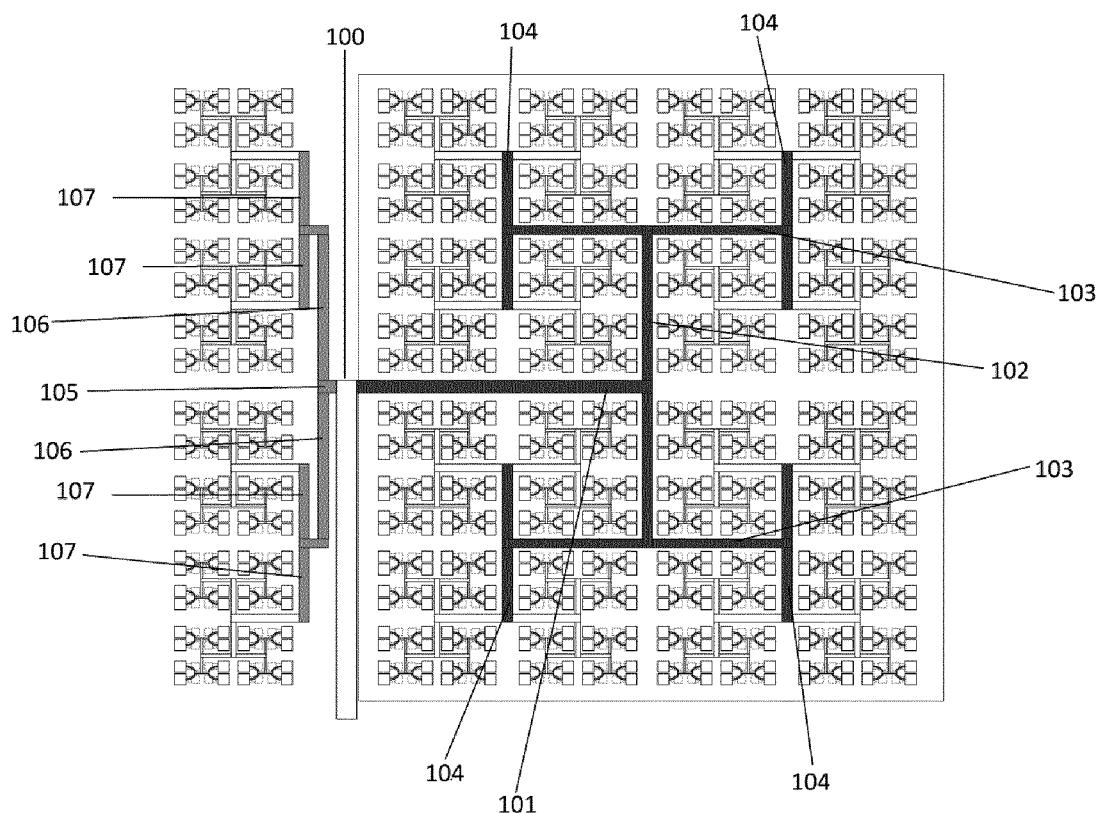
FIG. 10 shows schematically a plan view of a section of the chip of FIG. 9—in which the feed channels leading to two areas with different numbers of incubation segments are highlighted.

There are the following symmetries in this case:
i) The channels 101-104 and the channels 105-107 in FIG. 10 must have a volume proportional to $N_{right}$ and $N_{left}$ respectively which can be written as the following equation:

$$\frac{V_{channels_{101-104}}}{V_{channels_{105-107}}} = \frac{N_{right}}{N_{left}}.$$

ii) The other channels are shared by the same number of incubation segments.

Hence all such channels at both sides of the forking A are identical and their number scale up with the $N_{right}$ and $N_{left}$.

Conclusions 1.1. A chip with fractal geometry does not need any vacuum chamber 129 for even filling of all wells. Therefore, the required sample volume is equal to a sum of the volumes of the incubation wells with possibly a small reserve.

1.2. Uniform filling of the incubation segments does not require any specific controlling of a liquid flow. It is achieved by a thermal equilibrium and a pressure balance.

1.3. The required values of pressures can be easily applied with the use of vacuum pump. A filling deviation equal to or less than 5% does not affect the correct functioning of a chip.

1.4. The above derivation shows the optimal values of pressures. However, a pressure can be applied with some tolerance resulting from different occupation of the elements of the incubation segment ($V_A$-$V_D$) by an air, a sample and a non-aqueous liquid. These different configurations should ensure that a sample must not enter a gas cavity and that a gas and a non-aqueous liquid must not enter an incubation well. But such conditions leave certain margins for the $p_0$, $p_1$ and $p_2$ values according to the following formulas and specification:

$$p_{0min} = \frac{NV_D}{N(V_A + V_B + V_C + V_D) + V_{in} + V_{total}} p_{atm}$$

(gas fills the gas cavities only);

$$p_{0opt} = \frac{N\left(V_D + \frac{1}{2}V_C\right)}{N(V_A + V_B + V_C + V_D) + V_{in} + V_{total}} p_{atm}$$

(gas fills the gas cavities and a half of each gas exchange channel);

$$p_{0max} = \frac{N(V_D + V_C)}{N(V_A + V_B + V_C + V_D) + V_{in} + V_{total}} p_{atm}$$

(gas fills the gas cavities and gas exchange channels);

$$p_{1min} = \frac{NV_D}{N(V_A + V_C + V_D) + V_{in} + V_{total}} p_{atm}$$

(gas fills only the gas cavities, sample fills only the incubation wells);

$$p_{1opt} = \frac{N\left(V_D + \frac{1}{2}V_C\right)}{N\left(\frac{1}{2}V + \frac{1}{2}V + V_D\right) + V_{in} + V_{total}} p_{atm}$$

(gas fills the gas cavities and half of each gas exchange channel, sample fills incubation wells and halves of all gas exchange and inlet channels);

$$p_{1max} = \frac{NV_D}{NV_D + V_{in} + V_{total}} p_{atm}$$

(gas fills the gas cavities, sample fills the incubation wells and inlet and gas exchange channels);

$$p_{2min} = \frac{NV_D}{N(V_A + V_C + V_D) + V_{in}} p_{atm}$$

(gas fills the gas cavities, sample fills incubation wells and gas exchange channels, non-aqueous liquid fills inlet channels (or their parts—depending on pa) and the channels leading to the incubation segments);

$$P_{2opt} = \frac{N\left(V_D + \frac{1}{2}V_C\right)}{N\left(\frac{1}{2}V_A + \frac{1}{2}V_C + V_D\right) + V_{in}} p_{atm}$$

(gas fills the gas cavities and halves of gas exchange channels, sample fills incubation wells, halves of gas exchange channels and part of each inlet channel (depending on pa), non-aqueous liquid fills part of each inlet channel (depending on pa) and the channels leading to the incubation segments);

$p_{2max} = p_{atm}$ (gas fills the gas cavities and gas exchange channels, sample fills incubation wells and part of each intake channel (depending on $p_1$), non-aqueous liquid fills part of each inlet channel (depending on $p_1$) and the channels leading to the incubation segments).

The table below presents the exemplary values of a pressure defined as above which were calculated for a chip with asymmetric branches and 640 incubation segments accommodated. The following volumes are used $V_A$=0.36 µl, $V_B$=2.26 µl, $V_C$=0.26 µl, $V_D$=1.06 µl, $V_{in}$=0, and $V_{total}$=668.2 µl. Furthermore, $p_{atm}$ is assumed to be equal to 1013.25 mbar.

| | |
|---|---|
| $p_{0min}$ | 215.50 mbar |
| $p_{0opt}$ | 241.92 mbar |
| $p_{0max}$ | 268.35 mbar |
| $p_{1min}$ | 435.88 mbar |
| $p_{1opt}$ | 499.48 mbar |
| $p_{1max}$ | 510.46 mbar |
| $p_{2min}$ | 639.31 mbar |
| $p_{2opt}$ | 880.12 mbar |
| $p_{2max}$ | 1013.25 mbar |

FIGS. 11A to 11G show schematically lateral views of the steps of filing one incubation well of a chip.

Figure 11:
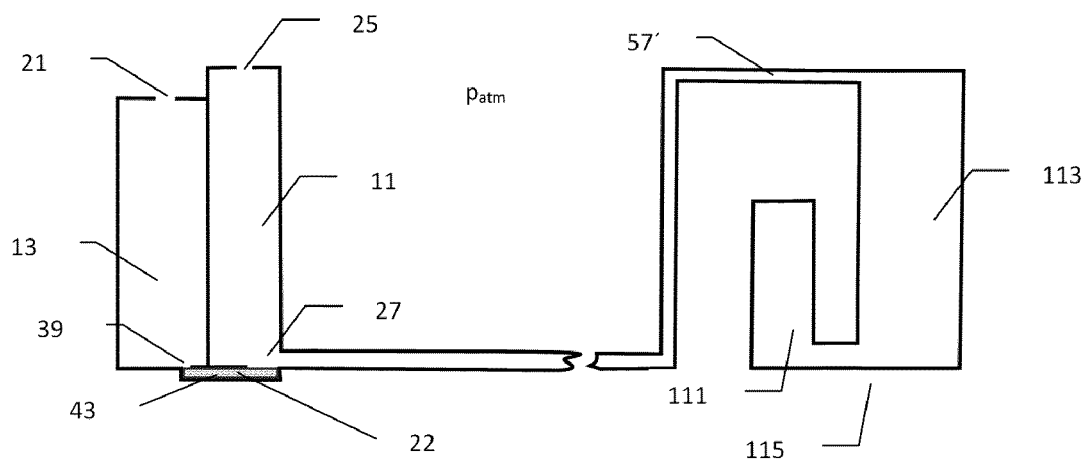
FIG. 11 shows schematically stages in a method according to the present invention for using a chip in accordance with the present invention.
Figure 11:
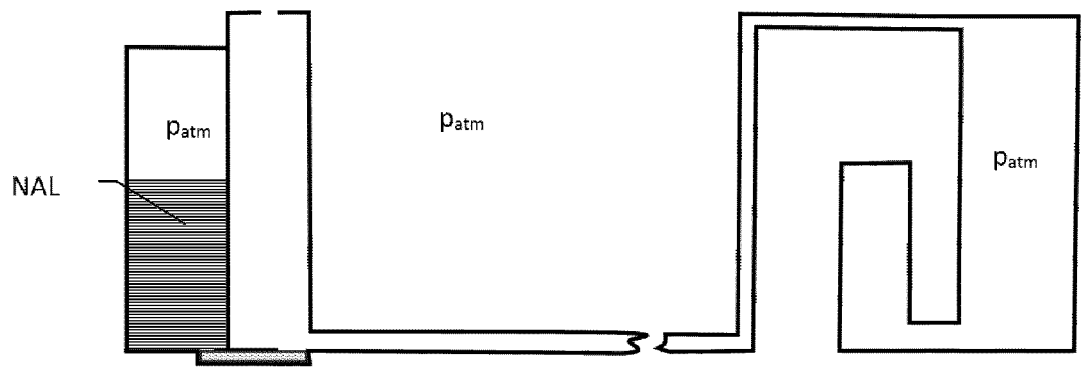
Figure 11:
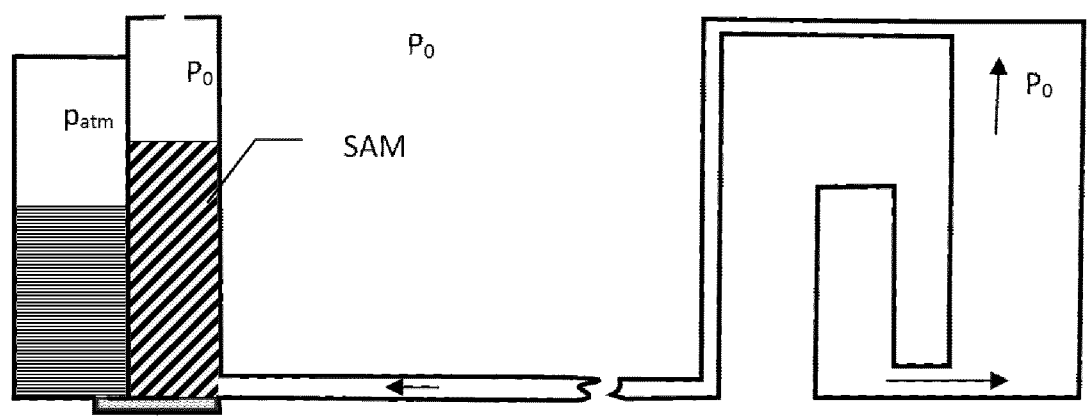
Figure 11:
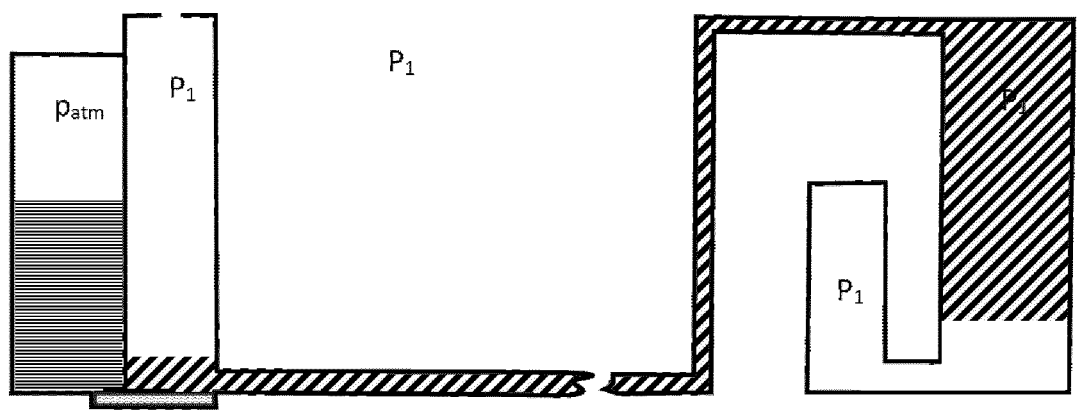
Figure 11:
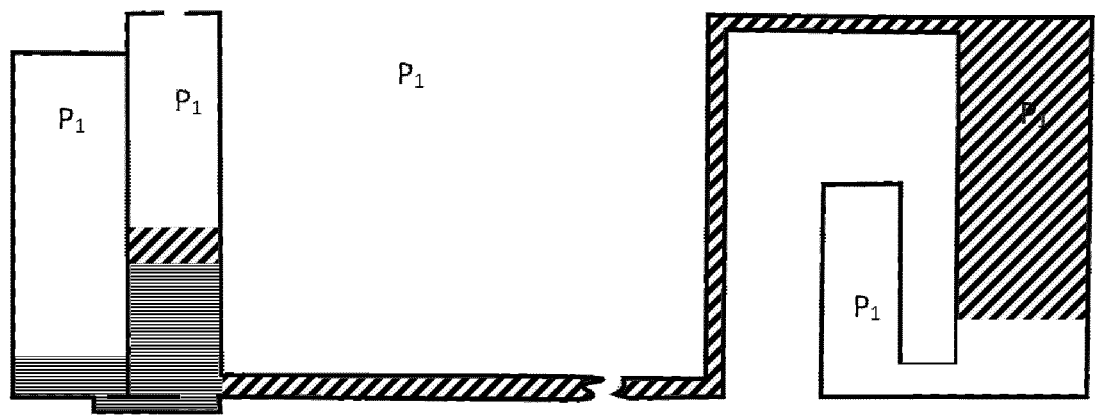
Figure 11:
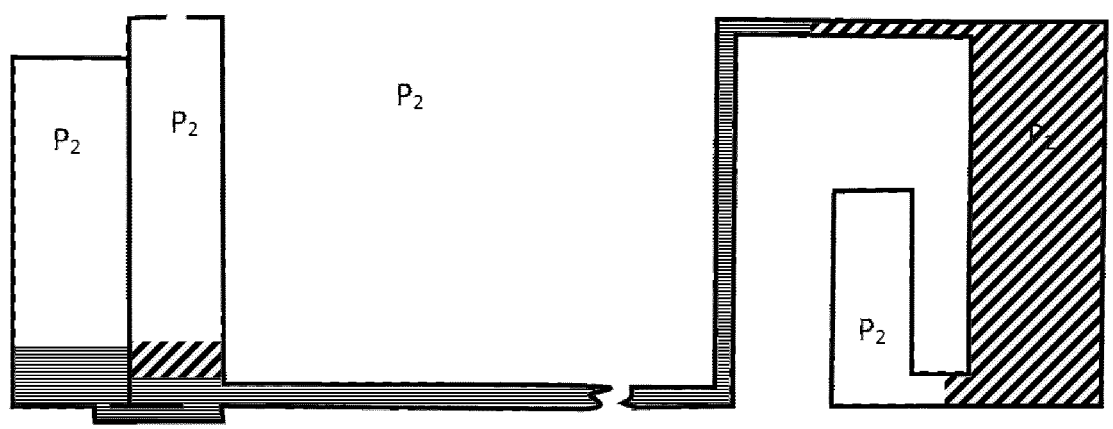
Figure 11:
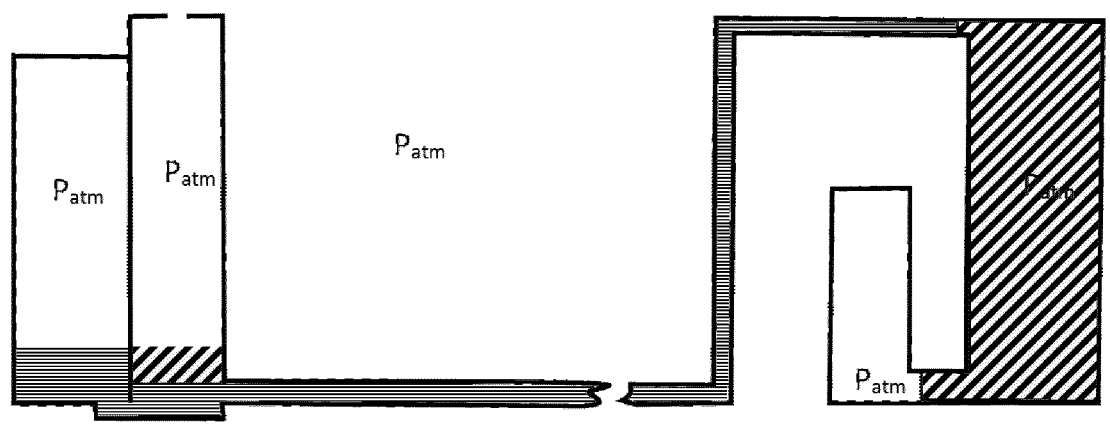

FIG. 11A shows schematically a portion of a chip. The chip comprises a sample reservoir for receiving and storing a sample for analysis 11, a non-aqueous liquid reservoir 13 for receiving and storing a non-aqueous liquid, a non-aqueous liquid inlet opening 21 leading to the non-aqueous liquid reservoir, a sample inlet passage 23 which leads to the sample reservoir, a sample reservoir outlet opening 27 leading to a passage 22, non-aqueous liquid reservoir outlet opening 39 leading to the passage 22, wax valve 24 which can prevent the non-aqueous liquid from leaving the non-aqueous liquid reservoir and entering the sample reservoir, a network of channels leading from the sample reservoir to the inlet channel 57' of an incubation segment 17', an incubation well 113 connected by a gas-exchange channel 115 to its associated unvented gas cavity 111. The ambient pressure around and inside the chambers and channels in the chip is atmospheric pressure $p_{atm}$.

In FIG. 11B the non-aqueous liquid reservoir has been partly filled with a non-aqueous liquid NAL and the inlet opening 21 sealed at atmospheric pressure.

In FIG. 11C the sample reservoir has been partly filled with a sample SAM. The inlet opening remains open to ambient pressure. Interplay between capillary and surface tension forces present at the entrance to the network of channels and the back-pressure of gas contained in the closed (unvented) microfluidic system downstream of the sample reservoir prevents the sample from entering the network of channels. The chip is placed in a chamber in which the pressure is then reduced to a pressure $p_o$ which is below atmospheric pressure. This causes expansion of the gas in the microfluidic system and causes some of the gas in the chip to flow out of the gas cavity, gas-exchange channel, incubation well, inlet channel and network of channels (the main microfluidic network) and to pass through the sample in the sample reservoir to the exterior of the chip until the pressure inside the microfluidic system is equal to $p_o$.

In FIG. 11D the pressure has been raised to $p_1$ which is higher than $p_0$. This pressure difference between upstream and downstream of the sample causes the sample to be pushed out of the sample reservoir into the microfluidic system, until the pressure inside the gas cavity, gas-exchange channel, incubation well, inlet channel and network of channels is substantially equal to $p_1$.

In FIG. 11E the valve between the non-aqueous liquid reservoir and the sample reservoir has been opened. As the pressure in the non-aqueous liquid reservoir is initially greater than $p_1$, the non-aqueous liquid in the non-aqueous liquid reservoir will flow from the non-aqueous liquid reservoir into the sample reservoir until the pressure in the non-aqueous liquid reservoir drops to $p_1$. Preferably the density of the non-aqueous liquid is greater than that of the sample, so that the excess sample floats on top of the non-aqueous liquid.

In FIG. 11F the ambient pressure is raised to $p_2$ which can be less than atmospheric pressure or equal to atmospheric pressure. The non-aqueous liquid is sucked into the network of channels and reaches the inlet channel 57' of an incubation segment 17', thereby preventing cross-contamination (cross-talk) between the incubation segment 17' and any neighbouring incubation segment.

FIG. 11G shows the continued penetration of non-aqueous liquid into the incubation segment if the pressure $p_2$ was less than atmospheric and which would occur when the chip is subjected to an ambient pressure equal to atmospheric pressure $p_{atm}$.

Figure 12:
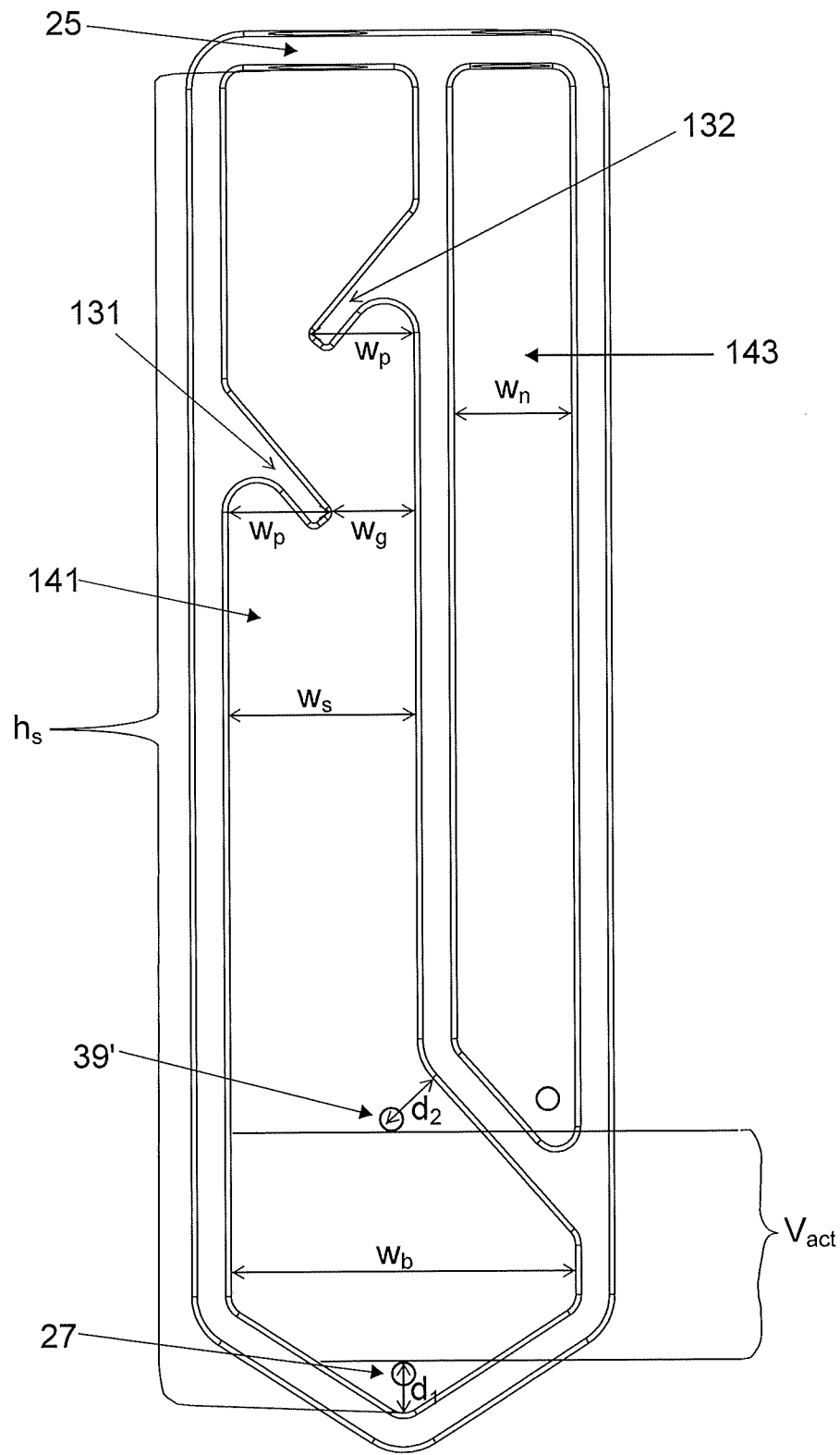
FIG. 12 shows a plan view of an embodiment of a sample reservoir and non-aqueous liquid reservoir in accordance with the present invention.

FIG. 12 shows a plan view of an embodiment of a sample reservoir 141 according to an embodiment of the present invention. The following paragraphs together with FIG. 12 describe preferred conditions for the proper operation of the sample and non-aqueous liquid reservoir according to the present invention. When the ambient pressure initially is decreasing, the gas from the microfluidic structure is evacuated from the interior of the chip by a pathway which flows through the sample in the reservoir. Optionally, loss of sample can be prevented by covering the sample inlet opening by a material which is impermeable for liquids after the sample has been loaded. Preferably this material is permeable to gas to allow gas to vent from the sample reservoir. As the sample inlet opening 25 need not necessarily be covered by a material impermeable for liquid during incubation segments filling (in fact it can even be open), it is desirable to provide means that help to ensure that the sample should not be lost through this opening. This can be achieved by making the vertical height $h_s$ of the sample reservoir large enough to give enough distance between the surface of a sample in the reservoir and the inlet opening to prevent leakage in normal use when the inlet opening is arranged higher than the outlet opening of the sample reservoir. Preferably the chip is loaded with sample and operated with the major surfaces of the substrate perpendicular to the horizontal and the inlet opening of the sample reservoir higher than the outlet of the sample reservoir. The height $h_s$ is preferably greater than or equal to 30 mm, more preferably greater than or equal to 40 mm, even more preferably greater than or equal to 50 mm. Furthermore, the prevention of sample leakage by being entrained by gas bubbles during the exiting of gas through the sample reservoir can be enhanced by providing the sample reservoir with one or more internal projections 131 and 132. These projections protrude from the side walls of the reservoir and prevent a sample from being pushed up by the gas bubbles flowing upward. They should be large enough to modify the cross-section of a channel through which the gas may flow and to change the shape of the bubbles. However, the distance between distal ends of the projections and the opposite side wall should also be greater than the distance across which capillary forces cause liquid flow, to prevent capillary forces affecting the sample there. Therefore, the width $w_s$ of the sample reservoir is preferably greater than or equal to 6 mm, more preferably greater than or equal to 7 mm, even more preferably greater than or equal to 9 mm. The width of the projection $w_p$ is preferably greater than or equal to 1 mm, more preferably greater than or equal to 2 mm, even more preferably greater than or equal to 3 mm. The width of the gap between the distal tip of the projection and the opposite side wall $w_g$ is preferably greater than or equal to 3 mm, more preferably greater than or equal to 4 mm. The sample reservoir can be broader at its lower (i.e. opposite to the sample inlet opening) end. This facilitates the evacuation of a gas and, for a given volume of sample, increases the distance from the exposed surface of the sample to the sample inlet opening compared to a narrow sample reservoir's lower end, which is helpful to prevent leakage. All width dimensions (i.e. perpendicular to a longitudinal axis of the sample reservoir) are relevant for these effects. Preferably the width, perpendicularly to the plane of the substrate, of the sample reservoir in the proximity of the lower end is greater than or equal to 5 mm, more preferably greater than or equal to 7 mm. Preferably the width in the plane of the substrate of the lower portion of the sample reservoir is greater than or equal to 10 mm. Those conditions significantly affect a volume of the sample reservoir. Its minimal value is equal to the product of the volume of single incubation well and the number of the incubation segments in the chip. Such a minimal volume is equal to or greater than 1.5 ml for a chip with 640 segments but is smaller for a smaller number of segments (for example about 0.29 ml for a chip with 128 segments). However, as can be seen from the above considerations, the volume of the sample reservoir should be larger. Preferably it is equal to or greater than twice the total volume of the incubation wells of all the incubation segments of the chip to which it is connected and more preferably it is equal to or greater than three times the total volume of said incubation segments.

The non-aqueous liquid (NAL) reservoir 143 should also have a volume which is larger than a minimal volume of NAL which is equal to the total volume of the microfluidic channels leading from the sample reservoir to all incubation segments. When a NAL flows to the sample reservoir after activation of a valve, the gas over the liquid should change its pressure from $p_{atm}$ to $p_1$ where $p_1$ is the pressure in the microfluidic chip when the sample flows into the incubation segments. In order to push out substantially the whole volume of NAL from the reservoir, its volume should not be smaller than $$\frac{p_{atm}}{p_{atm} - p_1} V_{NAL}$$

where $V_{NAL}$ the minimal volume of NAL mentioned above. Since $p_1$ can be about 0.67 $p_{atm}$ or less (it generally decreases with an increasing number of incubation segments), the NAL reservoir preferably has a volume equal to or greater than two times the total volume of the channels leading from the sample reservoir to all incubation segments, more preferably it is equal to or greater than three times said total volume. This reservoir should be also wide enough so that capillary forces do not prevent NAL flow to the sample reservoir. The reservoir width $w_n$ is preferably greater than or equal to 4 mm, more preferably greater than or equal to 5 mm, even more preferably greater than or equal to 6 mm. As a NAL enters the sample reservoir through the NAL outlet opening 39' and leaves it through the sample reservoir outlet opening 27, their proper positioning is important to minimize the dead volume of NAL. It is possible that the volume of the part of the sample reservoir enclosed between these openings, $V_{act}$, is greater than the minimal volume of NAL as defined above. The opening 27 preferably should be also located close to the lowest point of the sample reservoir, preferably at a distance $d_1$ which is smaller than or equal to 3 mm. It is also advantageous when a NAL entering the sample reservoir flows down the side of the sample reservoir. For this purpose, a distance $d_2$, which is smaller or equal to 3 mm, is preferred.

An embodiment of a chip according to the present invention has a substrate with a length of from 12 to 13.5 cm, preferably 12.8 cm length and a width of from 8 cm to 9 cm, preferably 8.5 cm, as described previously on page 14. Most preferably it has footprint dimensions of a microplate as specified in ANSI SLAS 1-2004 (R2012) "Footprint dimensions for microplates", namely 127.76 mm (with a tolerance of ±0.5 mm)×85.48 mm (with a tolerance of ±0.5 mm). Preferably it has a depth of from 0.19 to 0.22 cm, preferably 0.20 cm. Preferably, if the substrate is made of two parts joined together as described previously on page 9, then the base plate may have a thickness which is equal to or greater than 0.19 cm and less than or equal to 0.22 cm, and the reservoir portion a greater thickness, for example equal to or greater than 1 cm and equal to or less than 1.5 cm. A total of 640 incubation segments can be formed in this chip by choosing appropriate dimensions of the chambers and microchannels, and disposing them on both major faces of the substrate, e.g. as shown most clearly in FIGS. 1-2 and 6-9. Preferably, the volume of the sample reservoir is equal to or greater than 4 ml, less than or equal to 6 ml and more preferably 5 millilitres. Preferably, the volume of the non-aqueous reservoir is equal to or greater than 2.0 ml, less than or equal to 3.0 ml and more preferably 2.5 ml. Preferably, the total volume of the microfluidic channels is equal to or greater than 500 less than or equal to 900µl and more preferably about 668 µl. Preferably, each incubation segment has a volume which equal to or greater than 3.0 µl, less than or equal to 5.0 µl and more preferably about 3.94 µl. Preferably each incubation well has a volume equal to or greater than 2.0 µl, less than or equal to 2.50 µl and more preferably about 2.26 µl. Preferably each gas-exchange channel has a volume equal to or greater than 0.2 µl, less than or equal to 0.3 µl and more preferably about 0.26 µl. Preferably the unvented gas cavities each have a volume equal to or greater than 0.75 µl, less than or equal to 1.25 µl and more preferably a volume of about 1.06 µl.

The invention claimed is:

1. A microfluidic chip for conducting microbiological assays, comprising a substrate made of a first impermeable material with a first major face and a second major face, wherein a surface of the first major face is covered by a first layer of a second impermeable, substantially transparent material and a surface of the second major face is covered by a second layer of a third impermeable, substantially transparent material, and within the substrate are arranged:
a plurality of incubation segments each with an incubation segment inlet channel, a sample reservoir with a sample reservoir inlet opening and a sample reservoir outlet opening, and microfluidic channels connecting the sample outlet opening of said sample reservoir with each incubation segment inlet channel to said incubation segments, wherein said microfluidic chip further comprises a non-aqueous fluid reservoir for containing non-aqueous fluid, wherein said non-aqueous fluid reservoir has a fluid reservoir outlet opening which is connectable via a releasable airtight and liquid-tight valve with said microfluidic channels, wherein each incubation segment comprises an incubation well connected by a gas-exchange channel to an unvented gas cavity and the incubation segments are arranged in a fractal manner in which all respective microchannels of said microfluidic channels connecting each of the incubation segments to the sample reservoir are substantially equally long or have an equal resistance to flow or both.

2. The microfluidic chip of claim 1, wherein said microfluidic chip has a length from 12 cm to 13.5 cm, a width of from 8 cm to 9 cm, and a number of incubation segments is equal to or greater than 100 incubation segments.

3. The microfluidic chip of claim 1, wherein said microfluid chip is made of a polystyrene, a polycarbonate, a poly(methyl methacrylate), a cyclic olefin polymer or a cyclic olefin copolymer.

4. The microfluidic chip of claim 1, wherein said releasable airtight and liquid-tight valve is a heat-sensitive valve, comprising a wax valve which contains wax, which melts at a temperature greater than or equal to 37° C.

5. The microfluidic chip of claim 1, wherein at least one of two conditions are met: a volume of the sample reservoir is at least three times larger than a total volume of all the incubation wells of the microfluidic chip or a volume of the non-aqueous fluid reservoir is at least two times larger than a total volume of all the microfluidic channels leading from the sample reservoir to all of the incubation segments.

6. The microfluidic chip of claim 1, wherein the non-aqueous fluid reservoir has an inlet end and an outlet end and a width of the outlet end is narrower than a width of the inlet end, or a width of the non-aqueous fluid reservoir at its widest point is greater than or equal to 4 mm or both.

7. The microfluidic chip of claim 1, wherein a distance between the sample reservoir outlet opening and a lowest point of the sample reservoir, and a distance between an opening through which the non-aqueous fluid enters the sample reservoir and a nearest side wall of the sample reservoir are each equal to or less than 3 mm.

8. The microfluidic chip of claim 7, wherein the distance between the sample reservoir outlet opening and the lowest point of the sample reservoir, and the distance between the opening through which the non-aqueous fluid enters the sample reservoir and the nearest side wall of the sample reservoir are each equal to or less than 2 mm.

9. The chip of claim 1,
wherein all the incubation segments are substantially identical to one another and are connected in parallel,
wherein a summation of quotients of the volumes of all sections of the microfluidic channels leading from the sample reservoir to the incubation segment in question, and a number of incubation segments to which said microfluidic channel section lead is constant for all the incubation segments.

10. A method of filling of the incubation wells in the nnicrofluidic chip of claim 1, including the following steps in order:
a) providing, in said non-aqueous fluid reservoir, a non-aqueous fluid,
b) inputting a sample to the sample reservoir;
c) placing the microfluidic chip in a hermetically-sealed container separated from the surroundings of the hermetically-sealed container;
d) reducing a pressure in said hermetically-sealed container to a value $p_0$ to remove gas from the microfluidic chip;
e) increasing the pressure in said hermetically-sealed container to a value $p_1$, at which value $p_1$ the sample flows from the sample reservoir to the microfluidic channels connecting said sample reservoir with the incubation segments and further into said incubation segments;
f) activating the releasable and liquid tight valve to open a flow path from said non-aqueous fluid reservoir to said microfluidic channels connecting said sample reservoir with said incubation segments;
g) further increasing the pressure in said hermetically-sealed container to a value $p_2$, to force said non-aqueous fluid to flow into the microfluidic channels connecting the sample reservoir and said non-aqueous fluid reservoir with the incubation segments.

11. The method of claim 10, comprising the further step of subsequently further increasing the pressure in said hermetically-sealed container to ambient atmospheric pressure $p^{atm}$.

12. The method of claim 10, wherein said non-aqueous fluid has a viscosity greater than or equal to 20 cP, or in after step g, the nnicrofluidic chip is permanently sealed such that the interior of the nnicrofluidic chip is separated from the surrounding of the nnicrofluidic chip, or both.

13. The method of claim 12, wherein said viscosity of said non-aqueous fluid is greater than or equal to 50 cP.

14. A method of performing at least one microbiological assay using the nnicrofluidic chip of claim 1 the method comprising:
(1) filling the incubation wells in the microfluidic chip by performing the following steps in order:
a) providing, in said non-aqueous fluid reservoir, a non-aqueous fluid;
b) inputting a sample into the sample reservoir;
c) placing the microfluidic chip in a hermetically-sealed container separated from the surroundings of the hermetically-sealed container;
d) reducing a pressure in said hermetically-sealed container to a value $p_0$ to remove gas from the nnicrofluidic chip;
e) increasing the pressure in said hermetically-sealed container to a value $p_1$, at which value $p_1$ the sample flows from the sample reservoir to the microfluidic channels connecting said sample reservoir with the incubation segments and further into said incubation segments;
f) activating the releasable and liquid tight valve to open a flow path from said non-aqueous fluid reservoir to said microfluidic channels connecting said sample reservoir with said incubation segments;
g) further increasing the pressure in said hermetically-sealed container to a value $p_2$, to force said non-aqueous fluid to flow into the microfluidic channels connecting the sample reservoir and said non-aqueous fluid reservoir with the incubation segments; and
(2) performing at least one microbiological assay.

15. The method of claim 14, wherein said at least one microbiological assay comprises at least one of a group consisting of an identification of one or more microorganisms, a determination of a susceptibility to an antibiotic or to a combination of antibiotics, a determination of a minimum inhibitory concentration (MIC), and a detection of a mechanism of an antibiotic resistance.

* * * * *